US008021883B2

(12) United States Patent
Strøman

(10) Patent No.: US 8,021,883 B2
(45) Date of Patent: Sep. 20, 2011

(54) ANTIBIOTIC-SENSITIVE LACTIC ACID BACTERIA STRAINS

(75) Inventor: Per Strøman, Naerum (DK)

(73) Assignee: CHR. Hansen A/S, Horsholm (DK)

( * ) Notice: Subject to any disclaimer, the term of this patent is extended or adjusted under 35 U.S.C. 154(b) by 566 days.

(21) Appl. No.: 11/912,172

(22) PCT Filed: May 11, 2006

(86) PCT No.: PCT/DK2006/050020
§ 371 (c)(1),
(2), (4) Date: Jan. 22, 2008

(87) PCT Pub. No.: WO2006/119780
PCT Pub. Date: Nov. 16, 2006

(65) Prior Publication Data
US 2008/0171073 A1   Jul. 17, 2008

(30) Foreign Application Priority Data

May 11, 2005  (EP) ..................................... 05010216
Feb. 24, 2006  (DK) ........................... PA 2006 00267

(51) Int. Cl.
*C12N 15/01* (2006.01)
(52) U.S. Cl. ....................................... 435/441; 435/446
(58) Field of Classification Search ......................... None
See application file for complete search history.

(56) References Cited

U.S. PATENT DOCUMENTS 6,379,663 B1   4/2002   Gill et al.

FOREIGN PATENT DOCUMENTS

| AU | 673525 | 1/1996 |
|---|---|---|
| EP | 0 768 375 B2 | 10/1998 |
| WO | WO 97/16198 | 5/1997 |
| WO | WO 99/10476 | 3/1999 |
| WO | WO 01/97822 A1 | 12/2001 |
| WO | WO 03/099037 A1 | 12/2003 |

OTHER PUBLICATIONS

Ohta et al. (Mutation Res., 492:91-97, 2001).*
A.M. Yazid et al., "Antimicrobial susceptibility of bifidobacteria", Letters in Applied Microbiology 2000, 31, pp. 57-62.
Teresa M. Barbosa et al., "Evidence for recent intergeneric transfer of a new tetracycline resistance gene, tet(W), isolated from *Butyrivibrio fibrisolvens*, and the occurrence of tet(0) in ruminal bacteria", Environmental Microbiology, (1999) 1(1), 53-64.
Stephen J. Billington et al., "Widespread Distribution of a Tet W Determinant among Tetracycline-Resistant Isolates of the Animal Pathogen *Arcanobacterium pyogenes*", Antimicrobial Agents and Chemotherapy, May 2002, 1281-1287.
Yimin Cai et al., "*Bifidobacterium lactic* Meile et al. 1997 Is a Subjective Synonym of *Bifidobacterium animalis* (Mitsuoka 1969) Scardovi and Trovatelli 1974", Microbiol. Immunol. 44(10), 815-820, 2000.

Ian Chopra et al., "Tetracycline Antibiotics: Mode of Action, Applications, Molecular Biology, and Epidemiology of Bacterial Resistance", Microbiology and Molecular Biology Reviews, vol. 65, No. 2, Jun. 2001, pp. 232-260.
J.C. Deman et al., "A Medium for the Cultivation of *Lactobacilli*", J. Appl. Bact. 23, (1), (1960), pp. 130-135.
C. Garrigues et al., "Characterisation of *Bifidobacterium animals* subsp. *Lactis* BB-12 and other probiotic bacteria using genomics, transcriptomics and proteomics", The Australian Journal of Dairy Technology, vol. 60, No. 2, Jul. 2005, pp. 84-92.
Lydia Hung et al., "Megabase DNA Analysis: Chromosomal DNA Preparation, Restriction, and Pulsed-Field Electrophoresis", Promega Notes, No. 24, Apr. 1990, pp. 1-3.
List No. 62—"Validation of the Publication of New Names and New Combinations Previously Effectively Published Outside the USB", International Journal of Systematic Bacteriology, vol. 47, No. 3, Jul. 1997, pp. 915-916.
Michael A. Innis et al., "Optimization of PCRs", PCR Protocols a Guide to Methods and Applications, Academic Press Inc., 1990, pp. 3-12.
Morten Danielsen et al., "Susceptibility of *Lactobacillus* spp. to antimicrobial agents", International Journal of Food Microbiology 82 (2003) 1-11.
Liesbeth Masco et al., "Polyphasic taxonomic analysis of *Bifidobacterium animalis* and *Bifidobacterium lactis* reveals relatedness at the subspecies level: reclassification of *Bitidobacterium animails* as *Bifidobacterium animalis* subsp. *animalis* subsp. nov. and *Bifidobacterium lactis* as *Bifidobacterium animalis* subsp. *lactis* subsp. nov.", International Journal of Systematic and Evolutionary Microbiology (2004) 54, 1137-1143.
Leo Meile et al., "*Bifidobacterium lactis* sp. nov., a Moderately Oxygen Tolerant Species Isolated from Fermented Milk", System. Appl. Microbial. 20, 57-64 (1997).
Jeffrey H. Miller, "Experiments in Molecular Genetics—Experiment 33 Penicillin and Ampicillin Treatment for the Isolation of Auxotrophic Mutants", Cold Spring Harbor Laboratory, 1972, pp. 230-234.
"International Committee on Systematic Bacteriology Subcommittee on the taxonomy of *Bifidobacterium Lactobacillus* and related organisms", International Journal of Systematic and Evolutionary Microbiology (2001) 51, 259-261.
C. Moubareck et al., "Antimicrobial susceptibility of bifidobacteria", Journal of Antimicrobial Chemotherapy, (2005) 55, 38-44.

(Continued)

*Primary Examiner* — Nita M Minnifield
*Assistant Examiner* — Brian J Gangle
(74) *Attorney, Agent, or Firm* — Stephen A. Bent; Foley & Lardner LLP

(57) ABSTRACT

Many probiotic Bifidobacteriacea contains an active tetW that renders the cells resistant to tetracycline. This may present a risk of a horizontal transfer of functional antibiotic genes. The present invention relates to a method of obtaining novel tetracycline-sensitive strains of the genus of Bifidobacteriacea (*Bifidobacterium* sp.). In particular, the present invention relates to novel antibiotic-sensitive strains obtained from antibiotic-resistant probiotic strains and the use of such novel strains for the preparation of a food or feed product or a dosage form comprising viable organisms.

20 Claims, No Drawings

OTHER PUBLICATIONS

Martin Bastian Pedersen et al., "The long and winding road from the research laboratory to industrial applications of lactic acid bacteria", FEMS Microbiology Reviews 29, (2005) 611-624.

Karen P. Scott et al., "Occurrence of the New Tetracycline Resistance Gene *tet*(W) in Bacteria from the Human Gut", Antimicrobial Agents and Chemotherapy, vol. 44, No. 3, Mar. 2000, pp. 775-777.

"5—pH and Acidity", Microbial Ecology of Foods, vol. 1, Factors Affecting Life and Death of Microorganisms, 1980, pp. 92-111.

J.S. Zhou et al., "Antibiotic susceptibility profiles of new probiotic *Lactobacillus* and *Bifidobacterium* strains", International Journal of Food Microbiology 98 (2005) 211-217.

Susana Delgado et al., "Antibiotic Susceptibility of *Lactobacillus* and *Bifidobacterium* Species from the Human Gastrointestinal Tract", Curent Microbiology vol. 50, (2005), pp. 202-207.

Atte Von Wright, "Regulating the Safety of Probiotics—The European Approach", Current Pharmaceutical Design, 2005, 11, 17-23.

E. Kheadr et al., "Comparison of the sensitivity of commercial strains and infant isolates of bifidobacteria to antibiotics and bacteriocins", International Dairy Journal 14 (2004) 1041-1053.

R. Temmerman et al., "Identification and antibiotic susceptibility of bacterial isolates from probiotic products", International Journal of Food Microbiology 81 (2003) 1-10.

W.P. Charteris et al., "Antibiotic susceptibility of potentially probiotic *Bifidobacterium* isolates from the human gastrointestinal tract", Letters in Applied Microbiology 1998, 2, 333-337.

K.S. Lim et al., "Antimicrobial Susceptibility of Bifidobacteria", J Dairy Sci 76:2168-2174, 1993.

D. Matteuzzi et al., "Antimicrobial Susceptibility of *Bifidobacterium*", Ann. Microbial. (Inst. Pasteur) 1983, 134 A, 339-349.

William P. Charteris et al., "Gradient Diffusion Antibiotic Susceptibility Testing of Potentially Probiotic Lactobacilli", Journal of Food Production, vol. 64, No. 12, 2001, pp. 2007-2014.

Hiroshi Tanaka et al., "Bile Salt Hydrolase of *Bifidobacterium longum*—Biochemical and Genetic Characterization", Applied and Environmental Microbiology, vol. 66, No. 6, Jun. 2000, pp. 2502-2512.

Anna Piatkiewicz et al., "Influence of UV-Rays and Nitrosoguanidine on the Proteolytic Activity of *Lactobacillus casei*", Acta Alimentaria Polonica vol. IV(XXVIII), No. 2, 1978, pp. 217-228.

Mustafa Akcelik et al., "Turkiye'den Izole Edilen *Lactococcus lactis* subsp. lactis Suslarinda Nisin Uretim Ozelliginin Genetik Determinanlarinin Belirlenmesi", "Definition of Genetic Determinants of Nisin Production Ability in *Lactococcus lactis* subsp. Lactis Strains Isolated from Turkey", Tr. J. of Biology 20 (1996) 9-18.

Zhiqi Hao et al., "Characterization of Cadmium Uptake in *Lactobacillus plantarum* and Isolation of Cadmium and Manganese Uptake Mutants", Applied and Environmental Microbiology, vol. 65, No. 11, Nov. 1999, pp. 4741-4745.

Marilyn C. Roberts, "Update on acquired tetracycline resistance genes", FEMS Microbiology Letters 245 (2005) 195-203.

Janet Ash Tobian et al., "Characterization and Expression of a Cloned Tetracycline Resistance Determinant from the Chromosome of *Streptococcus mutans*", Journal of Bacteriology, vol. 160, No. 2, Nov. 1984, pp. 556-563.

Gianni Pozzi et al., "Host-Vector System for Integration of Recombinant DNA into Chromosomes of Transformable and Nontransformable *Streptococci*", Journal of Bacteriology, vol. 170, No. 4, Apr. 1988, pp. 1969-1972.

Lim et al; "Antimicrobial Susceptibility of Bifidobacteria"; Journal of Diary Science; vol. 76; No. 8; 1993; pp. 2168-2174.

\* cited by examiner

ANTIBIOTIC-SENSITIVE LACTIC ACID BACTERIA STRAINS

SEQUENCE LISTING

The instant application contains a Sequence listing which has been submitted in ASCII format via EFS-Web and is hereby incorporated by reference in its entirety. The ASCII copy, created on Apr. 6, 2011, is named 30427123.txt and is 34,355 bytes in size.

FIELD OF THE INVENTION

The present invention pertains to a method of obtaining novel antibiotic-sensitive strains of the genus of *Bifidobacterium* from antibiotic-resistant Bifidobacteriacea carrying a chromosomal encoded antibiotic resistance gene and the strains obtainable by the method. In particular, the present invention relates to novel antibiotic-sensitive strains obtained from antibiotic-resistant probiotic strains and the use of such novel strains for the preparation of a food or feed product or a dosage form comprising viable organisms.

BACKGROUND OF THE INVENTION

Bacteria which ferment sugars with the production of acids in particular lactic acid as a major metabolic component have been known for a long time. Such bacteria may be found in milk or milk products, living or decaying plants but also in the intestine of humans and animals. Traditionally, these bacteria have been referred to as "lactic acid bacteria". Lactic acid bacteria designate a rather heterologous group of Gram positive, non-motile, microaerophilic or anaerobic bacteria which ferment sugar with the production of acids including lactic acid and comprise e.g. the genera *Bifidobacterium, Enterococcus, Lactobacillus, Lactococcus, Leuconostoc* and *Pediococcus*.

For centuries lactic acid bacteria have been used in the manufacture of food and feed products including most dairy products, and today lactic acid bacteria are essential in the making of all fermented milk products such as yoghurt, cheese and butter. Furthermore, lactic acid bacteria are widely used in the meat processing industry, wine manufacturing industry, the juice manufacturing industry as well as a number of other industries.

Cultures of lactic acid bacteria also find important uses in the biopreservation of foodstuffs.

The publication of a large number of reports documenting that various lactic bacteria beneficially affect the well-being of humans and/or animals have attracted even further interest to this group of bacteria. In particular, specific strains of *Lactobacillus* or *Bifidobacterium* have been found to be able to colonize the intestinal mucosa and to assist in the maintenance of the well-being of the hosts.

EP 0 768 375 describes specific strains of *Bifidobacterium* ssp, that are capable of being implanted in the intestinal flora and being capable to competitively exclude adhesion of pathogenic bacteria to intestinal cells. These Bifidobacteria are reported to assist in immunomodulation and thus in the maintenance of the individual's health. The immunomodulation effect of Bifidobacteria may even be conferred onto unborn children. WO 01/97822, e.g. describes that intake of *Bifidobacterium animalis* strain Bb-12® by the mother during her pregnancy reduces the occurrence of atopic diseases in children. Also WO 03/099037 describes that *Bifidobacterium animalis* strain Bb-12® are able to beneficially modify the immune response. According to Masco et al. (2004), *Bifidobacterium animalis* strain Bb-12® should correctly be referred to as *Bifidobacterium animalis* subsp. *lactis* strain Bb-12®.

Probiotic microorganisms have been defined as "Live microorganisms which when administered in adequate amounts confer a health benefit on the host" (FAO/WHO 2002). During the recent years, documentation on probiotic properties of Bifidobacteria and other lactic bacteria has accumulated. In general, the probiotic activity is associated with specific strains. The previously mentioned *Bifidobacterium animalis* strain Bb-12® as well as *Bifidobacterium lactis* strain HN019 have been reported as probiotic (WO 01/97822, WO 03/099037, Zhou et al. (2005), U.S. Pat. No. 6,379,663).

Worldwide there is widespread public concern that the number of antibiotic resistant pathogenic bacteria increases dramatically. All available data indicate that the disturbing increase in antibiotic resistant pathogenic bacteria is caused by an extensive and very liberal use of antibiotics in the general population as well as in animal husbandry.

It is a well established fact that many antibiotic resistant bacteria carry genetic determinants, genes, which confer resistance to one or more antibiotics. It is furthermore wellknown that such genetic determinants under certain circumstances are transferable and may confer the antibiotic-resistant phenotype to recipient bacteria. The frequency of transfer is very much dependant on the particular genetic context in which the antibiotic resistance genes are found. I.e. antibiotic-resistant genes residing on plasmids or on transposons have been demonstrated to confer the antibiotic-resistant phenotype to recipient bacteria at relatively high frequencies, whereas chromosomally encoded determinants are very much less prone to move.

For these reasons it may be of concern to ingest even beneficial, non-patogenic bacteria if they do contain an antibiotic resistant determinant. This concern is further emphasized in the report from the EUROPEAN COMMISSION's Scientific Committee on Animal Nutrition (SCAN) on the Criteria for Assessing the Safety of Micro-Organisms Resistant to Antibiotics of Human Clinical and Veterinary of 3 Jul. 2001, revised on 24 Jan. 2003, stating that the presence of a known resistance gene is not acceptable (page 21).

Resistance to tetracycline is the most common bacterial antibiotic resistance found in nature and similarly is the most widely distributed type of resistance among bacteria isolated from animals (Billington 2002). Tetracycline inhibits protein synthesis by binding to a single high-affinity site on the 30S ribosomal subunit. With tetracycline in this position, the binding of aminoacyl-tRNA to the A site is prevented and thus protein synthesis is blocked.

Resistance to tetracycline may be mediated either by active efflux of tetracycline from the cell, by ribosomal protection by one or more soluble protein(s), the so-called ribosomal protection proteins (RPPs), or by enzymatic inactivation of tetracycline.

Recently, a new ribosome-protection-type tetracycline resistance ($Tet^r$) gene, tetW, was identified in rumen isolates of *Butyrivibrio fibrisolvens* and a number of other rumen bacteria (Barbosa, 1999).

Although the tetW determinant is widely distributed among tetracycline resistant isolates of animal pathogens (Billington 2002), it was a surprise for the authors of this application to find that all known probiotic strains of *Bifidobacterium animalis* subs. *lactis*, including the two well-known *Bifidobacterium* strains Bb-12® and DR10™, carry a functional tetW determinant and are resistant to tetracycline;

in particular because in a recent report the DR10™ strain as well as the Bb-12® strain were reported to be tetracycline sensitive (Zhou et al. 2005).

Even though extensive experiments have indicated that the tetW determinant of *Bifidobacterium animalis* subspecies *lactis* strain Bb-12® is not movable under realistic situations, the concern of antibiotic resistant determinants in food products still remains. Consequently, we have attempted several approaches to accomplish inactivation or removal of the tetW gene in *Bifidobacterium animalis* subspecies *lactis* Bb-12® by classical mutagenesis, involving various mutagens, as well as by direct genetic manipulation. However, until now all attempts have been unsuccessful. It is contemplated that an important reason to the many unsuccessful attempts is the fact that the tetW is located on the chromosome of probiotic *Bifidobacterium animalis* subs. *lactis* strains.

Thus it would be highly advantageous to establish a method for the inactivation of the tetW resistance gene in probiotic Bifidobacteriacea. Such method could furthermore help to solve the problem of providing antibiotic sensitive variants of commercial interesting probiotic, tetracycline resistant Bifidobacteriacea, that may meet the requirement of absence of functional antibiotic resistance genes.

SUMMARY OF THE INVENTION

The above problem has been solved by providing a method of isolating a tetracycline-sensitive strain of *Bifidobacterium* sp. (Bifidobacteriacea) from a tetracycline-resistant bacterial progenitor strain wherein the antibiotic resistant phenotype is caused by the expression of a functional tetW that is stably integrated in its chromosome, said method comprising subjecting the cells both to a chemical mutagen and a physical mutagen. Preferably, the chemical mutagen comprises ethidium bromide (EtBr) and the physical mutagen is UV.

This method appears generally applicable to tetracycline resistant *Bifidobacterium* sp. with a functional tetW stably integrated in their chromosome, as in each of the mutagenizing experiments that we have conducted with this method were able to isolate tetracycline sensitive variants of the two *Bifidobacterium* strains Bb-12® and HN019 (DR10™).

Thus, further important aspects of the invention are the provision of strains of *Bifidobacterium* sp. containing a mutated, chromosomally encoded tetW rendering the strain sensitive to tetracyclines, which is obtainable by the above mentioned method, and the use of such *Bifidobacterium* strains for the preparation of an ingestible material or a medicament.

In a first aspect the present invention relates to a method of inactivating a tetW gene in a *Bifidobacterium* sp. (Bifidobacteriaceae) cell, said method comprising subjecting a *Bifidobacterium* sp. cell comprising a functional tetW gene to a chemical mutagen and a physical mutagen.

In a second aspect the present invention relates to a method of preparing a *Bifidobacterium* sp. cell comprising an inactivated tetW gene, said method comprising the steps of:
a) inactivating a tetW gene in a *Bifidobacterium* sp. cell comprising a functional tetW gene by subjecting said cell to a chemical mutagen and a physical mutagen
b) isolating a mutant of the *Bifidobacterium* sp. cell obtained from step a) which has an inactivated tetW gene.

In a third aspect the present invention relates to a method of preparing a tetracycline sensitive *Bifidobacterium* sp. cell, said method comprising the steps of:
a) subjecting a *Bifidobacterium* sp. cell to a chemical mutagen and a physical mutagen, wherein the *Bifidobacterium* sp. cell has a Minimum Inhibitive Concentration of 4 microgram tetracycline/ml or higher
b) isolating a mutant of the *Bifidobacterium* sp. cell obtained from step a), wherein said mutant has a Minimum Inhibitive Concentration of 1.5 microgram tetracycline/ml or less.

In a fourth aspect the present invention relates to a *Bifidobacterium* sp. cell comprising an inactivated tetW gene.

In a fifth aspect the present invention relates a *Bifidobacterium* sp. cell which has a Minimum Inhibitive Concentration of 1.5 microgram tetracycline/ml or less.

In a sixth aspect the present invention relates to a *Bifidobacterium* sp. cell containing a mutated, chromosomally encoded tetW rendering the cell sensitive to tetracyclines obtainable by the method of the present invention.

In an seventh aspect the present invention relates to a *Bifidobacterium* cell which is sensitive to tetracyclines due to a mutation in tetW, said *Bifidobacterium* cell being derived from a progenitor cell which is resistant to tetracyclines due to the presence of a tetW gene located on the chromosome.

In an eight aspect the present invention relates to the use of a *Bifidobacterium* cell according to the present invention for the preparation of an ingestible material or a bacterial culture.

In a ninth aspect the present invention relates to a food or feed product comprising the bacterial cell of the present invention.

In a tenth aspect the present invention relates to a *Bifidobacterium* sp. cell according to present invention for the use as a probiotic.

In an eleventh aspect the present invention relates to a method of treating a mammal comprising administering a *Bifidobacterium* sp. cell according to present invention.

DETAILED DISCLOSURE OF THE INVENTION

In one embodiment the present invention relates to a method of inactivating a tetW gene in a *Bifidobacterium* sp. (Bifidobacteriaceae) cell, said method comprising subjecting a *Bifidobacterium* sp. cell comprising a functional tetW gene to a chemical mutagen and a physical mutagen.

The present invention further relates to a method of preparing a *Bifidobacterium* sp. cell comprising an inactivated tetW gene, said method comprising the steps of:
a) inactivating a tetW gene in a *Bifidobacterium* sp. cell comprising a functional tetW gene by subjecting a *Bifidobacterium* sp. cell comprising a functional tetW gene to a chemical mutagen and a physical mutagen.
b) isolating a mutant of the *Bifidobacterium* sp. cell obtained from step a) which has an inactivated tetW gene In a further embodiment the present invention also relates to a method of preparing a tetracycline sensitive *Bifidobacterium* sp. cell, said method comprising the steps of:
a) subjecting a *Bifidobacterium* sp. cell to a chemical mutagen and a physical mutagen, wherein the *Bifidobacterium* sp. cell has a Minimum Inhibitive Concentration of 4 microgram tetracycline/ml or higher
b) isolating a mutant of the *Bifidobacterium* sp. cell obtained from step a), wherein said mutant has a Minimum Inhibitive Concentration of 1.5 microgram tetracycline/ml or less.

The reason why it has been difficult to mutate a tetW gene in a *Bifidobacterium* sp. cell may be that the gene is located on the chromosome of the cells.

Thus, in a method of the present invention, the functional tetW gene may be located on the chromosome of the *Bifidobacterium* sp. cell.

Thus, in a method of the present invention the inactivated tetW gene may be located on the chromosome of the *Bifidobacterium* sp. cell.

The term "inactivated tetW gene" refers in the context of the present invention to a tetW gene which, if present in a cell, is not able to exert its normal function.

In particular an inactivated tetW gene is a gene which compared to a functional tetW gene comprises a mutation in the open reading frame (ORF) of the gene, wherein said mutation may be a frameshift mutation, introduction of a stop codon or a mutation which results in a non-conserved amino acid substitution. Non-conserved amino acid substitution is defined as a substitution of an amino acid residue for another amino acid residue with similar chemical properties (e.g. size, charge or polarity), which generally does not change the functional properties of the protein In particular, an inactivated tetW gene is a tetW gene which, when present in a cell, makes said cell sensitive to tetracycline.

The term "functional tetW gene" refers in the context of the present invention to a tetW gene which, if present in a cell, makes the cell resistant to tetracycline. In particular a functional tetW gene may be a gene comprising an open reading frame (ORF) which has a sequence corresponding to position 1318-3234 in SEQ ID NO:22 or a sequence which has 30%, such as 40% or 50% or 60% or 70% or 80% or 85% or 90% or 95% or 99% homology to the sequence corresponding to position 1318-3234 of SEQ ID NO: 22.

For purposes of the present invention, alignments of sequences and calculation of homology scores may be done using a full Smith-Waterman alignment, useful for both protein and DNA alignments. The default scoring matrices BLOSUM50 and the identity matrix are used for protein and DNA alignments respectively. The penalty for the first residue in a gap is 12 for proteins and 16 for DNA, while the penalty for additional residues in a gap is 2 for proteins and 4 for DNA. Alignment may be made with the FASTA package version v20u6 (W. R. Pearson and D. J. Lipman (1988), "Improved Tools for Biological Sequence Analysis", PNAS 85: 2444-2448, and W. R. Pearson (1990) "Rapid and Sensitive Sequence Comparison with FASTP and FASTA", Methods in Enzymology, 183: 3' or N-terminal->C-terminal direction of the nucleic acid or amino acid sequence, respectively.

It is a result of the present invention that the inventor is able to disclose a generally useful method for isolating a strain of *Bifidobacterium* sp. (Bifidobacteriacea) that contains a mutated tetW on its chromosome which renders the strain sensitive to tetracyclines and which is isolated from a tetracycline-resistant bacterial progenitor strain wherein the antibiotic resistant phenotype is caused by the expression of tetW stably integrated in its chromosome.

Reference to "progenitor strain" is in the present invention to be understood as reference to a *Bifidobacterium* sp. cell comprising a functional tetW gene, a tetracycline resistant *Bifidobacterium* sp. cell, or a *Bifidobacterium* sp. cell that has a MIC value of 4 microgram tetracycline/ml or higher.

Reference to "antibiotic sensitive strain" is in the present invention to be understood as reference to a *Bifidobacterium* sp. cell comprising an inactivated tetW gene, a tetracycline sensitive *Bifidobacterium* sp. cell, or a *Bifidobacterium* sp. cell that has a MIC value of 1.5 microgram tetracycline/ml or less.

In one embodiment of the present invention, the *Bifidobacterium* cell may be a strain.

In a further embodiment the methods of the present invention may after step a) further comprises the steps of:

i) transferring an aliquot of the UV treated culture to fresh medium containing a dose of a penicillin analogue which is detrimental to exponentially growing cells, but tolerable to non-growing cells, and
ii) culturing the cells in said penicillin analogue comprising medium under conditions, which would promote exponential growth in the absence of penicillin or an analogue of penicillin such as ampicillin.

The term "detrimental to exponentially growing cells" refers in the context of the present invention to compounds capable of reducing the exponential growth rate of the cells.

The term "tolerable" refers in the context of the present invention to compounds which are bacteriocritic.

In one embodiment, the methods of the present invention may comprise the steps of:

i) culturing the progenitor cells or the *Bifidobacterium* sp. cell comprising a functional tetW gene or that has a Minimum Inhibitive Concentration of 4 microgram of tetracycline/ml or higher to obtain a culture of exponential growing cells,
ii) transferring an aliquot of the cells obtained in step i) to fresh medium containing a chemical mutagen,
iii) transferring the culture obtained in step ii) to one or more containers to form a 0.5-10 mm thick layer of culture,
iv) subjecting the culture(s) of step iii) to a physical mutagen,
v) culturing the mutated cells obtained from step iv) to obtain a culture of exponential growing cells,
vi) transferring an aliquot bacteria from step v) to one or more Petri dishes containing a suitable agar growth medium, the aliquot of bacteria being selected to give single colonies
vii) identifying those colonies from step vi) that have acquired antibiotic sensitivity by replica plating to petridishes with and without antibiotic, and
viii) isolating and expanding the cells obtained in step vii).

The chemical and the physical mutagen may be as described in the paragraph describing chemical and physical mutagens which may be used in the methods of the present invention.

It may be an advantage keeping or storing the antibiotica sensitive colonies obtained in step viii).

This procedure may also be described as 1) culture the progenitor cells to obtain a culture of exponential growing cells, 2) transfer an aliquot of the cells to fresh medium containing ethidium bromide (EtBr), 3) transfer the culture to one or more containers to form a 0.5-10 mm thick layer of culture, 4) subject the culture to a UV treatment, 5) culture the mutated cells to obtain a culture of exponential growing cells, 6) transfer an aliquot of bacteria to one or more petridishes to form single colonies, 7) identify those colonies that have acquired antibiotic sensitivity by replica plating to petridishes with and without antibiotic, and 8) isolate, expand and keep those antibiotic sensitive colonies identified as a new antibiotic sensitive strain.

In a further embodiment the culture obtained in step iv) or 4) may be subjected to an enrichment step for mutations comprising the steps of:

iva) transferring an aliquot of the UV treated culture to a fresh medium containing a dose of a penicillin analogue which is detrimental to exponentially growing cells, but tolerable to non-growing cells, and
ivb) culturing the cells in said penicillin analogue comprising medium under conditions which would promote exponential growth in the absence of penicillin or an analogue of penicillin such as ampicillin.

In the art, dilution tests are used to determine the minimum inhibitory concentrations (MICs) of antimicrobial agents, and these are the reference methods for antimicrobial susceptibility testing. In dilutions tests, microorganisms are tested for their ability to produce visible growth in suitable media, and the lowest concentration of an antimicrobial agent that inhibits the growth of a microorganism is defined as the MIC. The terms Minimum Inhibitory Concentration, Minimum Inhibitive Concentration and MIC may be used interchangeably in the context of the present invention. The MIC (Minimum Inhibitory Concentration) may be regarded as the lowest concentration of a particular compound which results in inhibition of visible growth, or as the minimum concentration of the antibacterial agent in a given culture medium below which bacterial growth is not inhibited.

Different assays exist for determining the MIC value for a particular compound. In the context of the present invention, the MIC value may in particular be determined according to the Etest susceptibility screening method described by Danielsen and Wind (2003). The Etest susceptibility screening method comprises the steps of:
a) dipping a sterile cotton swab into a culture of a tetracycline sensitive strain to be tested, which has grown overnight,
b) streaking the entire surface of a MRS agar plate (diameter: 8.5 cm) evenly in three directions with the cotton swab from step a)
c) when the inoculum applied in step b) has dried, applying an E-test strip to the agar surface by help of a manual applicator with the MIC scale facing upwards
d) inoculating the agar plate under anaerobically or microaerophilic conditions in an inverted position at 37° C. overnight
e) determining the MIC value by reading the value where the edge of the inhibition ellipse intersects the strip.

This method and the Etest strip are also described in EP 157 071 which is incorporated herein by reference.

Yet another method for determining the minimum inhibitory concentration is disclosed in FR-A-2 264 089, which is incorporated herein by reference.

By the expression "tetracycline-resistant" refers to a bacterium which has a minimum inhibitory concentration (MIC) of tetracycline of at least higher than 4 ug/ml (EFSA, 2005), for instance at least 5 microgram/ml, such as at least 8 microgram/ml, including at least 10 microgram/ml or even at least 15 microgram tetracycline/ml. The MIC value may in particular be as determined by the Etest susceptibility screening method as described by Danielsen and Wind (2003).

Hence the *Bifidobacterium* sp. cell comprising a functional tetW gene may in particular have a Minimum Inhibitive Concentration as described above.

In the present context, the expression "sensitive to tetracyclines" refers to a bacterium which has a MIC of 1.5 microgram/ml or less, such as 1 microgram/ml or even less than 0.75 microgram/ml of a specific tetracycline of the group of tetracyclines. The MIC value may in particular be as determined by the Etest susceptibility screening method.

Specifically, the expression "sensitive to tetracycline" refers to a bacterium which has a MIC of 1.5 microgram tetracycline/ml or less, such as 1 microgram/ml or even less than 0.75 microgram tetracycline/ml. The MIC value may in particular be determined by the Etest susceptibility screening method.

Hence, the *Bifidobacterium* sp. cell comprising an inactivated tetW gene may in particular have a Minimum Inhibitive Concentration as described above.

As demonstrated in example 12, until now all mutations that are characterized by a minimum inhibitive concentration (MIC) determined by the E-test, which is equal to or less than 1.5 μg tet/ml, contained a mutated tetW. This opens for a selection procedure, which result in the selection of tetracycline-sensitive Bifidobacteria strains which, with a high probability, contains an inactivated tetW gene. Thus, the methods of the present invention may further comprise a selection of tetracycline-sensitive mutants that are particularly likely to contain a mutated tetW gene. This selection method may comprise the following steps, thus the step b) in the method of the present invention described above may in particular further comprise the steps of:
i) determining the minimum inhibitive concentration (MIC) of the bacteria by the Etest susceptibility screening method,
ii) dividing the bacteria into two classes based on the result of the Etest susceptibility screening:
   Class 1: bacteria with a MIC of 1.5 μg/ml or less according to the Etest, and
   Class 2: bacteria with a MIC over 1.5 μg/ml according to the Etest; and
iii) identifying and expanding the antibiotica sensitive bacteria identified in ii) with a MIC of 1.5 μg/ml or less (Class 1).

It may be a further advantage to keep the antibiotica sensitive bacteria obtained in step iii).

"Tetracyclines" or "tetracycline group of antibiotics" refer to the group of bactiostatic antibiotics that are produced by *Streptomyces* species, and their related semisynthetic derivatives. Tetracyclines inhibit both Gram-positive and Gram-negative bacteria and rickettsiae. They are characterized by a mode of action which imply that the antibiotic reversibly bind to the 30S ribosome and inhibit binding of aminoacyl-t-RNA to the acceptor site on the 70S ribosome. In addition to tetracycline itself, also terramycin, demeclocycline, meclocycline, doxycycline/doxycyclin, lymecycline, methacycline, minocycline, oxytetracycline, rolitetracycline, aureomycin as well as other chlortetracyclines are considered as members of the group of tetracyclines. Consequently, also a method wherein tetracyclines is an antibiotic selected from the group consisting of but not limited to tetracycline, terramycin, demeclocycline, meclocycline, doxycycline/doxycyclin, lymecycline, methacycline, minocycline, oxytetracycline, rolitetracycline, aureomycin and other chlortetracyclines is an embodiment of the present invention.

The preferred type of tetracyclines is tetracycline.

As mentioned, it required several attempts before the present method was developed. It is contemplated that it is the combined action of both a chemical and a physical mutagen, e.g. ethidium bromide and ultraviolet light, which increases the chance of a successful mutation of the tetW gene.

To further increase the likelihood of success, the culture or the *Bifidobacterium* sp. cell comprising a functional tetW gene or having a MIC value of 4 microgram tetracycline/ml or higher, may subsequent to the mutation step, i.e. the step of subjecting said culture or cells to a chemical and physical mutagen, be subjected to an enrichment step for mutations comprising the steps of: a) transferring an aliquot of the UV treated culture to fresh medium containing a dose of a penicillin analogue which is detrimental to exponentially growing cells, but tolerable to non-growing cells, and b) culturing the cells in said penicillin analogue comprising medium under conditions which would promote exponential growth in the absence of a penicillin analogue.

Considering that such an "ampicillin selection procedure" is well established and has been frequently used for gram-negative bacteria since 1972 (Miller 1972), it is surprising that the "ampicillin selection procedure" to the best of our knowledge has not previously been used in a mutation protocol directed against gram-positive Bifidobacteriaceae Although some Bifidobacteriacea may grow under aerobic conditions, it is considered advantageous when the culture is performed at a reduced oxygen tension, e.g. by supplying the growth medium with cysteine hydrochloride as described in example 1.

In general, the dual mutagenic approach of the present invention is considered more forceful scale than when the mutagens are used individually.

The chemical mutagen may in principle be any chemical compound capable of mutagenizing nucleic acids, in particular DNA. In particular the chemical mutagen may be an intercalating UV-absorbing mutagen, i.e. a chemical compound capable of both intercalating with nucleic acids, such as DNA, and of absorbing UV-light. Without being bound by any theory, the inventor of the present invention believes that by the combination of intercalating UV-absorbing compounds as chemical mutagens and UV irradiation as the physical mutagen, it is possible to obtain a certain degree of sequence-specificity with regard to mutation of a nucleic acid sequence, such as DNA. For example ethidium bromide (EtBr) which is an intercalating UV-absorbing compound does not usually intercalate randomly into DNA. Generally, the amount of EtBr which intercalates into the DNA depends on e.g. the degree of supercoiling of the DNA. As the degree of supercoiled DNA, at least in eukaryotes, correlates with the expression level of a particular gene, it is contemplated that this may result in a certain degree of sequence-specificity with regard to where the EtBr intercalates with the DNA. The presence of intercalated EtBr in a DNA sequence generally results in mutation(s) of the DNA sequence at the places where the EtBr is intercalated when said sequence is exposed to UV light. Furthermore, EtBr is generally to intercalate with in stretches of polydA-polydT tract DNA sequences or at least the ratio of EtBr intercalation with such sequences is low compared to other sequences.

Examples of suitable intercalating UV-absorbing compounds include, but are not limited to ethidium bromide (EtBr), ethidium, proflavine, daunomycin, adriamycin, actinomycin, ellipticine, tilorone, m-AMSA, mithramycin, netropsin, irehdiamine A, anthramycin, steptonigrin, bleomycin, ditercalinium, triostin and echinomycin. Other examples of such suitable compounds are given in U.S. Pat. No. 5,391,723, which is incorporated herein by reference.

The physical mutagen of the present invention may in a particular embodiment be a non-ionizing radiation with a wavelength shorter than 800 nm. An example of such a physical mutagen is UV radiation.

Hence, in one embodiment of the present invention, the chemical mutagen is an intercalating UV absorbing compound, such as any of the examples mentioned above, and the physical mutagen is a non-ionizing radiation with a wavelength shorter than 800 nm, such as UV radiation. In a further embodiment, the chemical mutagen is EtBr and the physical mutagen is UV radiation.

As illustrated in example 1, the combined action of EtBr and exposure to UV light considerably reduces the viability of the cells immediately after the EtBr-UV treatments. It is contemplated that such forceful dual approach may be the reason that it has been possible to achieve an effective inactivation of tetW gene in Bifidobacteriace. Thus in one important embodiment of the present invention, the UV-treatment is adjusted to result in a reduction of the number of living cells as measured by Colony Forming Units (CFUs) to less than 20%, such as less than 15% or even less that 10% relative to the number of the CFUs of the culture immediately before the UV-treatment. This adjustment of the UV-treatment may in one embodiment be performed in step iv) of the method.

In a preferred embodiment, the EtBr concentration is adjusted to be between 10 and 30 microgram/ml. In further embodiments, the penicillin analogue used in the "ampicillin enrichment procedure" is ampicillin which in particular may be used at a dose of 50-300 microgram/ml in the medium, in particular this dose of ampicillin may be used together with a EtBr concentration of 10-30 microgram/ml Resistance to tetracycline and oxytetracycline has been observed in strains of *Bifidobacterium catenulatum, Bifidobacterium longum, Bifidobacterium pseudocatenulatum, Bifidobacterium asteroids, Bifidobacterium infantis, Bifidobacterium lactis, Bifidobacterium animalis* and subspecies thereof (Yazid (2000), Lim (1983), Scott (2000), this study). TetW has been observed in tetracycline resistant strains of *Bifidobacterium longum, Bifidobacterium pseudocatenulatum, Bifidobacterium bifidum, Bifidobacterium lactis* (Scott et al. 2000, Moubareck et al. 2005). However, resistance to tetracycline is not characteristic of probiotic *Bifidobacterium* strains. Moubareck (2005) reports that probiotic Bifidobacteria in general appear to be more susceptible to antibiotics, and the two well-known probiotic Bifidobacteria, *Bifidobacterium animalis* subsp. *lactis* strain Bb-12® and DR10™ have been reported to be tetracycline sensitive (Zhou et al. 2005). Also, Moubareck (2005) did not find tetW in *Bifidobacterium animalis*. Surprisingly however; the present study has disclosed that also probiotic *Bifidobacterium* strains, including probiotic *Bifidobacterium animalis* strains such as *Bifidobacterium animalis* subsp. *lactis* strain Bb-12® and DR10™, contain a functional tetW rendering the bacteria resistant to tetracycline.

Thus, in presently preferred embodiments, the bacterial species is selected from the group consisting of Bifidobacteriacea that contains a functional tetW rendering the bacteria resistant to tetracycline. In a further preferred embodiment, the tetracycline-resistant bacterial progenitor strain is a probiotic strain. Similarly, the *Bifidobacterium* sp. cell comprising a functional tetW gene or that has a MIC value of 4 microgram tetracycline/ml or higher may be a probiotic cell.

The mutant *Bifidobacterium* sp. cell comprising an inactivated tetW gene or that has a MIC value of 1.5 microgram tetracycline/ml or less may also be a probiotic cell.

In the context of the present invention, the term "probiotic" is to be understood as "Live microorganisms which when administered in adequate amounts confer a health benefit on the host" (FAO/WHO 2002).

In particular, probiotic strains may be strains which are able to survive the passage of the esophagus and the stomach and furthermore able to survive the exposure to bile acid that occur in the upper part of the intestine. Consequently a potential probiotic bacterium is expected to survive exposure to the gastric juice in the stomach (example 9) and further exhibit resistance to bile salts (example 10). The placebo strain for such studies may in particular be strains which do not have a probiotic effect; more particularly strains which further do not have a pathogenic effect.

Other test for determining whether or not a strain is regarded as being probiotic include During the recent years, documentation of probiotic properties of Bifidobacteria and other lactic bacteria has accumulated. In general, the probiotic activity is associated with specific strains. The previously mentioned *Bifidobacterium animalis* strain Bb-12® as well as *Bifidobacterium lactis* strain HN019 have been reported as probiotic (WO 01/97822, WO 03/099037, Zhou et al. (2005), U.S. Pat. No. 6,379,663).

*Bifidobacterium* species which are useful in the present invention include but are not limited to *Bifidobacterium adolescentis*, *Bifidobacterium animalis*, *Bifidobacterium asteroids*, *Bifidobacterium bifidum*, *Bifidobacterium breve*, *Bifidobacterium catenulatum*, *Bifidobacterium infantis*, *Bifidobacterium lactis*, *Bifidobacterium longum* and *Bifidobacterium pseudocatenulatum* and subspecies thereof.

The invention is not, however, limited to these above mentioned particular Bifidobacteriacea. The person skilled in the art would recognise those Bifidobacteriacea which may be useful in the method according to the invention, as well as other probiotic bacteria which contain a functional tetW rendering them resistant to tetracyclines.

In the preferred embodiment, the progenitor strain or cell, the *Bifidobacterium* sp. cell which comprises a functional tetW gene or the *Bifidobacterium* sp. cell which has a MIC of 4 microgram tetracycline/ml or higher, is a strain of *Bifidobacterium animalis* subspecies *lactis*. In particular, said cell or strain is a cell or strain the *Bifidobacterium animalis* subspecies *lactis* strain CHCC5445 (Bb-12®), deposited on Sep. 30, 2003 according to the Budapest Treaty on the International Recognition of the Deposit of Microorganisms for the Purposes of Patent Procedure with the Deutsche Sammlung von Mikroorganismen und Zellkulturen under accession number DSM15954, or the *Bifidobacterium animalis* subspecies *lactis* strain CHCC7158, deposited on Apr. 28, 2005 according to the Budapest Treaty on the International Recognition of the Deposit of Microorganisms for the Purposes of Patent Procedure with the Deutsche Sammlung von Mikroorganismen und Zellkulturen under accession number DSM17280.

It is noteworthy to emphasise that the nomenclature of *Bifidobacterium animalis* sub-species *lactis* has changed over the years.

Initially, the *Bifidobacterium* Bb-12® strain was described as a *Bifidobacterium bifidum*. Subsequently it was found that *Bifidobacterium animalis* was more correct, although the strain is not a typical *Bifidobacterium animalis*. The strain differs in several aspects from *Bifidobacterium animalis* as described by Meile et al (1997), who suggested establishing a new species, *Bifidobacterium lactis*. This specie's name was later validated on list no. 62 in IJSB (1997). The species status of *Bifidobacterium lactis* has been discussed since Meiles publication. Recently, Cai et al. (2000) published DNA-DNA hybridisation results, which showed that *Bifidobacterium lactis* did not differ enough from *Bifidobacterium animalis* to allow species status. Based on these results, the International Committee on Systematic Bacteriology, Subcommittee on the taxonomy of *Bifidobacterium*, *Lactobacillus* and related organisms has decided that *Bifidobacterium lactis* cannot be acknowledged as a valid species (Minutes, IJSEM, 2001). Since then, a polyphasic taxonomic analysis has been done and published leading to the creation of two subspecies within *Bifidobacterium animalis* (Masco et al. 2004). Bb-12® belongs to one of the subspecies, *B. animalis* subsp. *lactis*. Based on DNA fingerprints, it appears to us that also the well-known *Bifidobacterium* strain DR10™ should correctly be designated as *B. animalis* subsp. *lactis*. In the literature strain DR10™, is also referred to as *Bifidobacterium lactis* HN019 (Zhou 2005) and HOWARU™ Bifido (www.danisco.com).

As illustrated in example 2, the method of the present invention may result in two classes of novel antibiotic-sensitive isolates one class which express an intermediate level of tetracycline sensitivity, i.e. isolates with a MIC ranging between 2 and 4 µg tetracycline/ml, and isolates with a MIC lower than 1.5 µg tetracycline/ml such as 0.75 or even 0.5 µg tetracycline/ml. Until now, we have only identified isolates with an inactivated tetW in isolates with a MIC lower than 1.5 µg tetracycline/ml, and in all cases we used Bifidobacteriacea having a MIC larger than 10 microgram tetracycline/ml as progenitor cells. Thus, a preferred embodiment of the present invention is a method of isolating a tetracycline sensitive strain of *Bifidobacterium* sp. (Bifidobacteriacea) from a tetracycline-resistant bacterial progenitor strain wherein the Minimum inhibitive Concentration (MIC) of tetracycline of the progenitor strain is at least 10 microgram tetracycline/ml and the MIC of the antibiotic sensitive strain is 1.5 microgram tetracycline/ml or less. The progenitor strain may be a *Bifidobacterium* sp. cell comprising a functional tetW gene or that has a MIC value of 4 microgram tetracycline/ml or higher, and the antibiotic sensitive strain may be a mutant *Bifidobacterium* sp. cell comprising an inactivated tetW gene or that has a MIC value of 1.5 microgram tetracycline/ml or less.

As the tetracycline group of antibiotics shares the same mode of action, it is contemplated that the inactivation of tetW in general will result in a sensitivity shift to any of the tetracycline group of antibiotics of a size similar to the shift observed with tetracycline. Consequently, an embodiment of the invention is a method of isolating a strain of *Bifidobacterium* sp. (Bifidobacteriacea) that is sensitive to one or more of tetracyclines from a bacterial progenitor strain that is resistant to one or more of the tetracyclines and wherein the Minimum inhibitive Concentration (MIC) of said antibiotic of the progenitor strain is at least 10-fold higher than the MIC of the antibiotic sensitive strain. The progenitor strain may be a *Bifidobacterium* sp. cell comprising a functional tetW gene or that has a MIC value of 4 microgram tetracycline/ml or higher, and the antibiotic sensitive strain may be a mutant *Bifidobacterium* sp. cell comprising an inactivated tetW gene or that has a MIC value of 1.5 microgram tetracycline/ml or less.

Examples of the tetracycline group of antibiotics are represented by the group of antibiotics comprising tetracycline, terramycin, demeclocycline, meclocycline, doxycycline/doxycyclin, lymecycline, methacycline, minocycline, oxytetracycline, rolitetracycline, aureomycin and other chlortetracyclines.

To the best of our knowledge, until now all probiotic strains of *Bifidobacterium animalis* subs. *lactis*, and a substantial number of other Bifidobacteriacea carry a functional tetW determinant rendering them resistant to tetracycline. The inventor of the present invention surprisingly discovered that it was possible to provide Bifidobacteriacea that carry an inactivated tetW determinant.

As illustrated in the examples, it is indeed possible to obtain variants of known probiotic strains of *Bifidobacterium* sp. that contains a mutated, chromosomally encoded tetW rendering the strain sensitive to tetracyclines. The provision of such new strains is considered the most preferred embodiment of the present invention.

Hence in a further embodiment, the present invention relates to a *Bifidobacterium* sp. cell comprising an inactivated tetW gene. This cell may in particular have a Minimum Inhibitive Concentration of 1.5 microgram tetracycline/ml.

In a further embodiment, the *Bifidobacterium* sp. cell the inactivated tetW gene may be located on the chromosome of said cells.

In another embodiment, the present invention also relates to a *Bifidobacterium* sp. cell which has a Minimum Inhibitive Concentration of 1.5 microgram tetracycline/ml.

In a further embodiment, the present invention relates to a *Bifidobacterium* sp. cell containing a mutated, chromosomally encoded tetW rendering the cell sensitive to tetracyclines obtainable by a method of the present invention.

The present invention also relates to a *Bifidobacterium* cell which is sensitive to tetracyclines due to a mutation in tetW, said *Bifidobacterium* cell being derived from a progenitor cell which is resistant to tetracyclines due to the presence of a tetW gene located on the chromosome.

The new strain or cell may in principle be a variant or mutation of any *Bifidobacterium* that carries a chromosomally encoded tetW rendering the strain resistant to tetracyclines. Suitable cells may be selected from the group of Bifidobacteriacea comprising *Bifidobacterium longum*, *Bifidobacterium pseudocatenulatum*, *Bifidobacterium bifidum*, *Bifidobacterium lactis*, *Bifidobacterium animalis* and subspecies thereof. In particular, cells classified as *Bifidobacterium animalis* subspecies *lactis* are preferred.

Reference to tetracycline in relation to a *Bifidobacterium* sp. cell of the present invention include those described in relation to the methods of the present invention. Similarly, the progenitor cell may be any of those previously mentioned in relation to a progenitor cell useful in a method of the present invention.

In general, new bacterial strains having a Minimum inhibitive Concentration (MIC) of antibiotic which is at least 10-fold lower than the MIC of the antibiotic resistant progenitor strain are preferred.

Hence, the Minimum inhibitive Concentration of antibiotic (MIC) of the progenitor cell may be at least 10-fold higher than the MIC of the antibiotic sensitive cell.

In particular, the Minimum inhibitive Concentration (MIC) of tetracycline of the progenitor cell may be at least 10 microgram tetracycline/ml and the MIC of the antibiotic sensitive strain cell may be 1 microgram tetracycline/ml or less.

Preferred *Bifidobacterium* sp. cells of the present invention may be those having a MIC that is 1.5 microgram tetracycline/ml or less, such as 1 microgram/ml or even less than 0.75 microgram tetracycline/ml. The MIC value may in particular be as determined by the Etest susceptibility screening method.

Such strains which harbor a mutated tetW are particularly preferred embodiments of the invention.

The inactivating mutation of the tetW gene that renders the new strains sensitive to tetracyclines may typically be described in relation to the tetW gene sequence of the relevant progenitor cell.

As described in the examples suitable tetracycline-sensitive strains with an inactivated tetW can be achieved by introducing specific mutations in the tetW gene.

In one preferred embodiment of the invention, an "opal" stop codon has been introduced in the tetW by changing a part of the chromosomally encoded tetW characterized by the sequence TCG CTG GGA TAC TTG AAC CAG AGT [SEQ ID 1] to TCG CTG GGA TAC T$\overline{GA}$ ACC AGA GTT [SEQ ID 2], the deleted base in the functional tetW is indicated by underscoring. Thus, a *Bifidobacterium* cell which comprises the sequence: GGA TAC TGA ACC [SEQ ID 3] or [ATACT-GAA] in its tetW gene is a preferred embodiment of the present invention. We also observed that the tetW gene could be inactivated, and result in sensitivity to tetracycline, by changing the part of chromosomally encoded tetW which comprises the sequence: CAG AGC GTG GTT CAG TCT GTT CGG [SEQ ID 4] to CAG AGC GTG GTT$\overline{TAG}$ TCT GTT CGG [SEQ ID 5]. This mutation introduces an "amber" stop codon in tetW, and the mutated base in the functional tetW is underscored. Such a *Bifidobacterium* which comprise the sequence: GTG GTT TAG TCT [SEQ ID 6] or [GGTT-TAGT] in its tetW gene is another preferred embodiment of the present invention. A bacterial strain or the *Bifidobacterium* sp. cell of the present invention wherein the inactivated or mutated tetW gene comprises at least one sequence selected from the group consisting of but not limited to SEQ ID NO:3 [GGA TAC TGA ACC], [ATACTGAA], SEQ ID NO: 6 [GTG GTT TAG, TCT], [GGTTTAGT], SEQ ID NO: 27 [AC CAG CGT TTT C] and [CAGCGTTT] is also an embodiment of the present invention.

The introduction of the "opal" and the "amber" stop codons into the protein coding region of the tetW gene represents two very different molecular events. I the case of the "opal" mutation, a base was deleted, whereas in the case of the amber, a base was mutated (in casu from C to T pair, i.e. a base transition).

It should be emphasized that the tetW of a *Bifidobacterium* may be inactivated by other types of mutations in other sites of tetW. This is illustrated by the *Bifidobacterium* mutant strain Bb-12Tet-S180 wherein the tetW gene comprise SEQ ID NO: 27 [AC CAG CGT TTT C] which represents a single-base transversion of an A to a C in position #2731 in SEQ ID 22; and the DR10Tet-S33 and Bb-12Tet-S79 which comprise multiple mutations in tetW. DR10Tet-S33 comprise two mutations in tetW described by SEQ ID NO: 28 [CG CCC TGC CAC A] (or [CCCTGCCA]) and SEQ ID NO: 29 [AT ATT GTC ATC A] (or [ATTGTCAT]), and Bb-12Tet-S79 comprise three mutations described by SEQ ID NO: 30 [TA GAC GAT GGA A] (or [GACGATGG]), SEQ ID NO: 31 [CG GTC CGG GTA A] (or [GTCCGGGT]) and SEQ ID NO: 32 [CT GAT CCG GCC TT] (or [GATCCGGC]). Thus in one embodiment, the *Bifidobacterium* sp. cell of the present invention may be a cell wherein the inactivated or mutated tetW gene comprises one of the above mentioned combinations of sequences.

Thus, the *Bifidobacterium* sp. cell according to the present invention may be a cell, wherein the inactivated or mutated tetW gene comprises at least one sequence selected from the group of SEQ ID 3 [GGATACTGAACC], SEQ ID NO: 6 [GTGGTTTAGTCT], [ATACTGAA], SEQ ID NO: 27 [AC-CAGCGT TTTC], SEQ ID 28 [CGCCCTGCCACA], SEQ ID 29 [ATATTGTCATCA], SEQ ID 30 [TAGACGATG-GAA], SEQ ID 31 [CGGTCCGGGTAA], SEQ ID 32 [CT-GATCCGGCCTT], [CAGCGTTT], [GACGATGG], [GTC-CGGGT], [ATCCGGCC], [CCTGCCAC], [TTGTCATC], [GGTTTAGT], [GTGGACCG], [CGCCCATT] and [TCCG-GCCC].

In particular, the *Bifidobacterium* sp. cell according to the present invention may be a cell wherein the inactivated or mutated tetW gene comprises the sequences [CCTGCCAC] and [TTGTCATC].

In another embodiment, the *Bifidobacterium* sp. cell according to the present invention may be a cell wherein the inactivated or mutated tetW gene comprises the sequences [GACGATGG], [GTCCGGGT] and [ATCCGGCC].

Insofar as the *Bifidobacterium* strain contains a mutated, chromosomally encoded tetW rendering the strain sensitive to tetracyclines and which is obtainable by the method of the present invention, the resulting tetracycline sensitive strains are embodiments of the present invention.

A very important indication of whether a mutated tetracycline sensitive strain is particularly likely to contain a mutated tetW gene, is to determine minimum inhibitive concentration (MIC) of the bacteria by the Etest susceptibility screening method. As demonstrated in example 12, mutated strains may be classified in two classes: Class 1: strains with a MIC of 1.5 μg/ml or less; and Class 2: strains with a MIC >1.5 μg/ml. This is used in an embodiment of the method of isolating strains which comprise the steps of:

a) determining the minimum inhibitive concentration (MIC) of the bacteria by the Etest susceptibility screening method,
b) based on the result of the Etest susceptibility screening, dividing the bacteria into two classes:
   Class 1: bacteria with a MIC of 1.5 µg/ml or less according to the Etest, and
   Class 2: bacteria with a MIC over 1.5 µg/ml according to the Etest; and
c) identifying and expanding those antibiotics sensitive bacteria identified in b) to belong to class 1.

In a further embodiment step c) may include keeping the antibiotics sensitive bacteria. In particular step c) may be identifying, expanding and keeping those antibiotica sensitive bacteria identified in b) to belong to class 1 as a new antibiotics sensitive strain. The most preferred embodiment of the present invention is the bacterial strain or the *Bifidobacterium* sp. cell of the present invention, which is identified as *Bifidobacterium animalis* subspecies *lactis* strain CHCC8902 (Bb-12Tet-S139) and deposited on Apr. 28, 2005 according to the Budapest Treaty on the International Recognition of the Deposit of Microorganisms for the Purposes of Patent Procedure with the Deutsche Sammlung von Mikroorganismen und Zellkulturen under accession number DSM17281. This tetracycline sensitive strain contains the "opal" mutation in its tetW. This strain is particularly preferred because it is a mutation of the well-known probiotic *Bifidobacterium* strains Bb-12®. Furthermore, CHCC8902 contains a single base deletion in tetW characterized in a relatively low reversion rate of less than $1.6 \times 10^{-9}$ making it particularly suitable for ingestion in large numbers (see Example 4). As illustrated in example 9 and 10, the tetracycline sensitive Bb-12Tet-S139 strain has preserved the characteristics of a probiotic strain. Thus, in a particularly preferred embodiment of the present invention, the tetracycline-sensitive bacterial strain or the *Bifidobacterium* sp. cell of the present invention is a probiotic strain.

Another preferred embodiment of the present invention is a bacterial strain or the *Bifidobacterium* sp. cell of the present invention which is identified as *Bifidobacterium animalis* subspecies *lactis* strain CHCC9070 (DR10Tet-S9X) and deposited on Apr. 28, 2005 according to the Budapest Treaty on the International Recognition of the Deposit of Microorganisms for the Purposes of Patent Procedure with the Deutsche Sammlung von Mikroorganismen und Zellkulturen under accession number DSM17282. This tetracycline sensitive strain contains the "amber" mutation in its tetW. This strain is also preferred because it is a mutation of the well-known probiotic *Bifidobacterium* strain DR10™ (CHCC7158). CHCC9070 (DR10Tet-S9X) contains a single base transition in tetW. As anticipated by the existing literature on base transitions, the reversion rate is higher than e.g. deletion mutants. In the case of CHCC9070 which contains the back mutation rate $1.8 \times 10^{-8}$. Although CHCC9070 is more prone to reversion than CHCC8902, the strain is still relatively stable and consequently suitable for ingestion.

As mentioned, some Bifidobacteria can serve as probiotics i.e. as non-pathogenic organisms, which have health benefits when taken orally in foods or capsules. Common targets of probiotic action are intestinal disorders (e.g. travelers diarrhea, antibiotic associated diarrhea) or intestinal symptoms (bloating, flatulence, discomfort). Yet, a wider range of benefits (e.g. anticholesterolemic, anticarcinogenic and immunostimulatory properties) is also discussed in the probiotic literature.

Thus in a further embodiment, the present invention relates to the use of a *Bifidobacterium* sp. cell of the present invention for the preparation of an ingestible material or a bacterial culture.

Thus in a further embodiment, the *Bifidobacterium* sp. cell of the present invention may be for the use as a probiotic.

In particular the *Bifidobacterium* sp. cell of the present invention for the use as a probiotic may be in the form of an ingestible material.

In another embodiment, the present invention also relates to a method of treating a mammal by administering a *Bifidobacterium* sp. cell according to the present invention.

In particular the *Bifidobacterium* sp. cell may be given in the method as an ingestible material.

The terms "gastrointestinal tract" or "intestinal" are in the present context used interchangeably and relate to both the upper and lower gastrointestinal tract which include the mouth, the oesophagus, the stomach, the small intestines including the duodenum, the jejunum and the ileum, and the large intestines comprising colon and caecum.

The bacterial culture may in a further embodiment be further processed.

The bacteria, i.e. the *Bifidobacterium* sp. cell, of this invention may be given in the form of a fermented food product or in a dosage forms formulated as a tablet (including chewable tablets), a capsule (of either the hard or soft type), a powder, a granulate, a liquid preparation, a suspension, a dried oral supplement, a wet oral supplement, a dry tube feeding formulation or wet tube feeding formulation.

In one embodiment, the ingestible material is a fermented food or feed product pre-pared by use of the Bifidobacteria of the present invention. Hence in another embodiment the present invention also relates to a food or feed product comprising a bacterial cell or strain according to the present invention, i.e. a *Bifidobacterium* sp. cell according to the present invention.

The fermented food or feed product may be further processed. In a number of situations, it has been reported that bacteria produce health promoting compounds during fermentation. In such cases, it might be advantageous to fractionate and/or up concentrate fractions of the fermented food product. One can even imagine that it, in certain situations, would be valuable to further process the fermented food product by pasteurization, even though the beneficial Bifidobacteria are inactivated by such procedure. However, in general it is considered beneficial that the ingestible material comprise live Bifidobacteria in an amount from about $10^5$ cfu/g to about $10^{12}$ cfu/g ingestible material, since living cells are a prerequisite for obtaining the probiotic effect.

It is contemplated that the Bifidobacteria of the present invention can be used for the preparation of a wide range of ingestible materials such as milk, curd, milk based fermented products, acidified milk, yoghurt, frozen yoghurt, milk powder, milk based powders, milk concentrate, cheese, cheese spreads, dressings beverages, ice-creams, ice-lollies or popsicles, fermented cereal based products, infant formulae and soybean milk.

A further important embodiment of the present invention is the use of the Bifidobacteria of the present invention to prepare a composition for the treatment or prevention of a disease, syndrome or condition, or for improving digestion of nutrients, or for improving the general health status of a human being or a vertebrate animal.

Since Bifidobacteria in general are considered as probiotic organisms (Yazid, 2000) the use of a Bifidobacteria of the present invention as a probiotic is a preferred embodiment. The probiotic composition of the present invention can be any ingestible material selected from the group consisting of milk, curd, milk based fermented products, acidified milk, yoghurt, frozen yoghurt, milk powder, milk based powders, milk concentrate, cheese, cheese spreads, dressings beverages, ice-creams, fermented cereal based products, infant formulae, tablets, liquid bacterial suspensions, dried oral supplement, wet oral supplement, dry tube feeding or wet tubefeeding that are produced by use of the Bifidobacteria of this invention.

In a further embodiment, the composition further comprises a pharmaceutically acceptable carrier. As used herein, the term "pharmaceutically acceptable carrier" means one or more solid or liquid filler diluents, or one or more encapsulating substances which are suitable for administration to a human or an animal and which is/are compatible with the probiotically active organisms. The term "compatible" relates to components of the pharmaceutical composition which are capable of being comingled with the probiotic in a manner enabling no interaction because it would substantially reduce the probiotic efficacy of the organisms selected for the invention under ordinary use conditions. Pharmaceutically acceptable carriers must be of a sufficiently high purity and a sufficiently low toxicity to render them suitable for administration to humans and animals being treated.

In useful embodiments, the ingestible material according to the invention is suitable for preventing or treating a disease, syndrome or condition selected from the group consisting of antibiotic-associated disorders, gastroenteritis, diarrhea including traveler's diarrhea and acute infantile diarrhea, lactose intolerance, gastrointestinal infections and colonization of the gastrointestinal tract by pathogenic bacteria including *Helicobacter pylori* and *Clostridium difficile*, irritable bowel syndrome (IBS), inflammatory bowel disease (IBD) and other immunomodulative syndromes, colonic cancer, urogenital infections and tumours, vaginal infections, allergy (especially atopic eczema), vaccination, cholesterolemia and hypertension.

In further useful embodiments, the ingestible material according to the invention is suitable for preventing or treating infections with pathogens such as e.g. *Heliobacter pylori, Campylobacter pylori, Staphylococcus aureus, Staphylococcus epidermidis, Streptococcus pyogenes, Streptococcus pneumoniae, Enterococcus faecalis, Hemophilus influenzae, Escherichia coli, Klebsiella pneumoniae, Enterobacter cloacae, Citrobacter freundii, Serratia marcescens, Pseudomonas aeruginosa* and *Pseudomonas maltophilia, Salmonella* sp. and fungi such as *Candida albicans* and *Aspergillus fumigatus*, and combinations of these species.

In recent years, rotaviruses and other enteric viruses have been identified as a major cause of infectious diarrhoea. Interestingly, both *Bifidobacterium* Bb-12® and HN019 (DR10™) have been shown to effectively prevent or treat infections also with these pathogens. Thus, in useful embodiments, the ingestible material according to the invention is used for preventing or treating infections with rotaviruses and other enteric viruses.

It may be useful to combine two or more of the above assumingly probiotically active organisms, such as e.g. a preparation comprising a Lactobacillus species and a *Bifidobacterium* species.

Performance of the Mutant Strains and their Benefits to Human

The *Bifidobacterium animalis* subsp. *lactis* Bb-12® (CHCC5445), is an extremely important strain for the health and well being of mammals due to its probiotic capabilities (e.g. immune stabilizing effect in humans, controlling of a balanced microflora in the digestive tract thereby reducing or acting as inhibitors of various epidemiologic syndromes, etc.). Also the *Bifidobacterium animalis* subsp. *lactis* HN019 (DR10™, CHCC7158), has an impressive record of probiotic activity. Although both of these strains harbours an active gene encoding resistance to tetracycline, the most prominent bacterial antibiotic resistance found in nature (Chopra and Roberts, 2001), both have for many years been used in food production, and to our knowledge without causing any harm. On the contrary, only positive effects have been ascribed to the use of these strains. However, the fact that both strains contain an active tetW in their genome does possess the theoretical possibility of transferring the tetracycline resistance to other—and perhaps harmful bacteria in the human digestive system. The risk of this increase if ingested donor bacteria survive in the gut in large numbers, as is the case with the typical use of probiotic bacteria. Inactivation of the tetW gene in the two variants, as it has been demonstrated here, eliminates the risk of a horizontal transfer of functional antibiotic resistant genes. Apart from the lesion in the tetW, the two tetracycline sensitive strains are probably isogenic with their mother strains, as suggested under Example 5 and Example 6. Thereby it can be assumed that the two tetracycline sensitive strains possess most if not all the features that make Bb-12® and HN019 (DR10™) probiotic.

In addition, laboratory tests involving two-dimensional gel-electrophoresis for further characterization of the mutant strains are being performed to verify the isogenic background with the wild type strains.

CONCLUSION

1) —inactivation of the tetracycline resistance gene, tetW, from *Bifidobacterium animalis* ssp *lactis* Bb-12® and *Bifidobacterium animalis* ssp *lactis* HN019 (DR10™) was established by a combination of the intercalating mutagen, ethidium bromide, and successive ultra violet irradiation.

2) —five of the resulting tetracycline sensitive isolates originating from Bb-12® and from HN019 (DR10™) were incapable of growing in MRS broth with tetracycline in a concentration above 1.5 µg/ml.

3) —characterization of one of the mutant isolates, Bb12Tet-139 (a derivative of CHCC5445) demonstrated a frame shift at nucleotide position #2722 in the tetW gene immediately resulting in an opal stop codon 170 amino acids short of the gene product. In the other mutant, DR10Tet-S9X (a derivative of CHCC7158) an amber stop codon was introduced (nucleotide position #1741), 498 amino acids short of the gene product.

4) —the reversion rate for Bb12Tet-S139 is less than $1.6 \times 10^{-9}$ and the back mutation rate for DR10Tet-S9x is $1.8 \times 10^{-8}$.

5) —growth, acidification rates DNA-profile and the transcriptome (Example 6) of the tetW mutants were not different to the respective wild types strains.

6) —analyses of the mutant isolates did not disclose any re-arrangements or modifications, but for tetW, of the genomic DNA as judged from DNA fingerprinting- and transcriptomics analyses 7) —experiments show that Bb12Tet-139 have preserved many of the probiotic characteristics of Bb-12®.

Bifidobacteria and other lactic acid bacteria are commonly used as starter cultures serving a technological purpose in the production of various foods. The most well known industry using starter cultures is the dairy industry, but starter cultures are also used in other industries, e.g. in the meat processing industry. Thus, one embodiment of the pre-sent invention is the use of a *Bifidobacterium* strain according to the invention for the preparation of a starter culture. Starter cultures may be provided as frozen or dried starter cultures in addition to liquid starter cultures. In a further embodiment the starter culture may be freeze dried, spray dried or fluid bed dried.

A starter culture composition according to the invention typically comprises bacteria of a concentration of viable cells, which is in the range of $10^4$ to $10^{12}$ cfu per gram of the composition. A convenient method of making a frozen starter culture comprising the following steps: 1. culturing a bacterial strain according to present invention, 2. harvesting the propagated cells to provide a concentrated bacterial culture, 3. freezing the bacterial material to get frozen material, and 4. packing the freeze dried material in a suitable container. Similarly, a convenient method of making a freeze dried starter culture comprises the following steps: 1. culturing a bacterial strain according to claims present invention, 2. harvesting the propagated cells to provide a concentrated bacterial culture, 3. freezing the bacterial material to get frozen material, 4. sublimation of water from the frozen material, and 5. packing the freeze dried material in a suitable container. Also, a spray/fluid bed dried starter culture is contemplated. The freezing of the bacterial material may conveniently be performed by dripping the concentrated culture into liquid nitrogen and collecting the frozen material.

As disclosed in WO 2005/003327 A1, it is beneficial to add certain cryoprotective agents to a starter culture. Thus, a starter culture composition according to the present invention may comprises one or more cryoprotective agent(s) selected from the group consisting of inosine-5'-monophosphate (IMP), adenosine-5'-monophosphate (AMP), guanosine-5'-monophosphate (GMP), uranosine-5'-monophosphate (UMP), cytidine-5'-monophosphate (CMP), adenine, guanine, uracil, cytosine, adenosine, guanosine, uridine, cytidine, hypoxanthine, xanthine, hypoxanthine, orotidine, thymidine, inosine and a derivative of any of such compounds.

The invention is illustrated in the following non-limiting examples and tables, wherein Table 1 is a description of oligonucleotides used for PCR analyses and DNA sequencing of the tetracycline resistance-encoding tetW gene of Bb-12® and HN019.

Table 2 is the tetW DNA sequence and the upstream transposase gene, tps, from *Bifidobacterium animalis* subsp. *lactis* Bb-12® (SEQ ID 22). The nucleotide sequence of the TetW gene and flanking region from *Bifidobacterium animalis* subsp. *lactis* Bb-12®. The sequence was obtained by sequencing at Chr. Hansen AIS. Upstream is the transposase encoding open reading frame, nt. #4-966, with the amino acid depicted under the DNA sequence (M. W. approx. 35 kDa). The nt. sequence #1318-3234 is the tetracycline resistant encoding gene, tetW, with the amino acid outlined under the DNA sequence. (M. W. approx. 70 kDa).

The amber mutation at nucleotide (nt) position #1741 (nt #424 relative to the start codon of tetW) for the tetracycline sensitive strain, DR10Tet-S9X (CHCC9070), is indicated above the DNA sequence. The frameshift mutation at nt position #2722 (nt #1405 relative to the start codon) for the tetracycline sensitive strain, Bb12Tet-S139 (CHCC8902), is indicated above the DNA sequence.

*): indicates a stop codon.

Table 8-1: List of reference strains used to verify the specific detection of Bb-12Tet-S139.

Table 9-1: Conditions for stability testing of freeze-dried cultures.

Table 9-2: Survival of freeze-dried cultures (%).

Table 10-1. Survival in artificial gastric juice (%). Average of three experiments Table 11-1. Tolerance to bile acids. Bacterial growth on MRS-Cystein HCl agar plates supplemented with 2% w/v bile salts.

Table 12-1. Minimum inhibitory concentrations (MICs) of tetracycline of probiotic strains of *Bifidobacterium animalis* subspecies *lactis* and two derivatives thereof.

Table 13-1. Minimum inhibitory concentrations (MICs) of tetracycline Bb-12 and 3 new derivatives thereof.

EXAMPLES

Example 1

Inactivation of the tetW Gene in Two Probiotic Strains of *Bifidobacterium animalis* Subspecies *lactis* Expressing Resistance to Tetracycline A strong and dual mutagenic approach was used to inactivate the intrinsic tetracycline resistance of the genome of *Bifidobacterium animalis* ssp. *lactis* strain Bb-12® and strain HN019 (DR10™). This included treatment of the cells with the mutagen, ethidium bromide (EtBr) followed by ultra violet irradiation in a more forceful scale than normal when the mutagens are used individually.

Strains and Culture Conditions.

Strains of *Bifidobacterium animalis* subspecies *lactis* Bb-12® and HN019 (DR10™) were obtained from the culture collection of Chr. Hansen A/S, Hørsholm, Denmark. *B. animalis* subsp. *lactis* strain Bb-12® has the accession number CHCC5445 in the Hansen culture collection, and is deposited with the Deutsche Sammlung von Mikroorganismen und Zellkulturen (DSMZ) under accession number DSM15954. *B. animalis* subsp. *lactis* strain HN019 (DR10™) was isolated from a commercially available infant formula product labeled Fernleaf DR-10 bifidus and sold in Taiwan during 2000. It has the accession number CHCC7158 in the Hansen culture collection and is deposited with DSMZ under accession number DSM17280.

The two strains that are resistant to tetracycline (at least 15 µg/ml, as determined by the E-test procedure, Danielsen and Wind, 2003), were grown routinely under anaerobically conditions at 37° C. in Difco-MRS broth (deMan 1960), supplied with 0.05% Cysteine hydrochloride (Cysteine-HCl, Merck chemicals) as well as on MRS agar (1.5% agar) with the same concentration of Cysteine-HCl and 15 µg of tetracycline per ml.

Mutagenic Treatment of Bb-12

An aliquot (2%) of a Bb-12® grown overnight (on) in MRS was transferred to fresh MRS broth (10 ml without tetracycline) containing 20 µg/ml ethidium bromide (EtBr) and incubated to optical density [OD] at 600 nm, 0.35. The exponentially growing cells were then subjected to UV-irradiation (UV cross-linker, Stratagene) in an open Petri dish for 5 min (70 mJ/cm$^2$). The UV treatment was repeated once after a dark interval of 5 min at room temperature. The treatment was adjusted to obtain a lethality of approximately 90%. The lethality was assessed as follows: The viability of the cells immediately after the EtBr-UV treatments was determined by cell plating on MRS agar without tetracycline and the lethality was calculated from the observed CFU.

One ml of the mutagenised culture was then transferred to 9 ml fresh MRS without the addition of EtBr and was then allowed to grow for a period of 16 hours at 37° C. in complete darkness, at which point aliquots of the treated cells were

Example 2

Selection of Tetracycline-Sensitive Variants of Two Probiotic Strains of *Bifidobacterium animalis* Subspecies *lactis*

Screening Procedure

Screening for tetracycline sensitive isolates was performed after an ampicillin enrichment procedure (Miller, 1972) adapted to Bifidobacteriae was performed. Briefly, the ampicillin enrichment procedure was performed by transferring an aliquot (1%) of the out-grown mutagenized culture to fresh MRS medium (10 ml) and growing the cells to an $OD_{600}$ of 0.2 without the addition of tetracycline. 0.5 ml of this culture was used to inoculate 10 ml of MRS broth containing 10 microgram tetracycline/ml and incubated for 2 hrs at 37° C. at reduced oxygen tension, after which ampicillin was added to a final concentration of 150 microgram/ml, and the culture was continuously incubated for 16 hrs at 37° C. As ampicillin only kills growing cells (i.e., $Tet^R$ cells) and not nondividing cells (i.e. mutant $Tet^S$ cells), the addition of ampicillin can be considered an enrichment step for the subsequent isolation of $Tet^S$ mutants. Cells were harvested by centrifugation (4,000×G for 5 min at 4° C.) and washed twice with fresh MRS broth.

Following the ampicillin enrichment, the screening for tetracycline sensitive isolates was performed by plating aliquots of the washed cells on MRS agar in an appropriate dilution to give approximately 150 colonies per plate after incubation at 37° C. for 20 hours.

Tetracycline sensitive colonies were identified by replica plating on MRS agar without antibiotics and MRS agar containing 10 µg of tetracycline per ml, on which the tetracycline sensitive isolates were unable to grow. Finally, the tetracycline sensitive colonies were cultured in MRS broth. Total genomic DNA was isolated from both the tetracycline sensitive clones and the tetracycline resistant strain for intensive characterization. The replica screening resulted in 155 tetracycline sensitive isolates from CHCC5445 of a total of approximately 4,000 screened colonies. From CHCC7158, 43 tetracycline sensitive colonies were isolated out of approximately 1,000 cells. All these colonies were further tested in liquid MRS broth containing tetracycline (10 µg/ml). A substantial fraction of false positives (approx. 85%) managed to grow under these conditions. The remaining tetracycline sensitive isolates were then subjected to E-test susceptibility screening to determine their tetracycline sensitive threshold.

The E-test was performed according to the method of the manufacturer (AB BIODISK, Sweden), slightly modified by M. Danielsen and A. Wind (2003), Briefly, determination of the Minimum Inhibitory Concentration (MIC) value for the individual isolates was performed by dipping a sterile cotton swab into an overnight culture of the tetracycline sensitive strain to be tested and to streak the entire surface of a MRS agar plate (diameter: 8.5 cm) evenly in three directions. After dryness of the applied inoculum, an E-test strip was applied to the agar surface by help of a manual applicator with the MIC scale facing upwards. Plates were inoculated anaerobically overnight in an inverted position at 37° C. The MIC value was determined by reading the value where the edge of the inhibition ellipse intersects the strip. In most cases it ranged between 2 and 4 µg/ml. Only two isolates, one derived from CHCC5445, named Bb12Tet-S139, and one derived from CHCC7158, named DR10Tet-S9X, demonstrated a higher sensitivity to tetracycline with a MIC value of 0.5 µg/ml.

Example 3

Molecular Characterization of the Tetracycline-Sensitive Derivatives of Two Probiotic Strains of *Bifidobacterium animalis* Subspecies *lactis*

PCR Amplification and DNA Sequencing of the tetW Gene

Genomic DNA was prepared from wild type Bb-12® and the two tetracycline-sensitive isolates by the use of the Easy-DNA protocol for isolation of DNA from gram-positive bacteria according to the manufacturer's (Qiagen) instructions.

The tetW gene of the sensitive variants was characterized by PCR analyses according to the protocol of Innis and Gelfand (1990) and DNA sequenced to test for possible mutations in that gene. The entire open reading frame (ORF, approx. 2.0 kb) of tetW was amplified from each isolate in three overlapping fragments (A, B and C) with three sets of primers (table 1, table 2).

Fragment A (approx. 785 bp) was amplified with sense primer: tetWx.D1, derived from a sequence 296 bp upstream of the start codon of the tetW gene and antisense primer: tetWx.R2, derived from the ORF of tetW. Fragment B (approx. 935 bp) was amplified with sense primer: tetWx.D4 and antisense primer: tetWx.R5 of the ORF of tetW Fragment C (920 bp) was amplified with sense primer: TetWx.D3 derived from the ORF and antisense primer: tetWx.R4 262 bp downstream of the termination codon of the tetW gene.

The amplified fragments from the three PCR reactions were subjected to agarose gel-electrophoresis (0.7%) and staining in EtBr and identified with UV illumination. The bands corresponding to the three amplified gene fragments were excised from the gel and DNA extracted (QIAquick gel extraction kit from Qiagen). The purified PCR products were cloned into the plasmid vector, pCR2.1-TOPO (Invitrogen), for nucleotide sequence determination using the M13 forward and reverse primers.

DNA sequencing of the tetW genes from each of the individual tetracycline sensitive isolates with E-test-values of 2-4 µg/ml demonstrated that the tetracycline resistance gene was not affected or mutated in these isolates, and was 100% homologous to the tetW gene in the wild type Bb-12® depicted in Table 2.

Sequencing of the tetW genes from the two isolates with tetracycline E-test-values of 0.5 µg tetracycline/ml showed that in both cases the tetW gene was affected. The Bb12Tet-S139 (a derivative of CHCC5445) demonstrated a frameshift at nucleotide position #2722, where a thymidine residue was deleted as illustrated below and in table 2.

```
                                                         (SEQ ID NO: 33)
Amino acid sequence:         - Ser Leu Gly Tyr Leu Asn Gln Ser (SEQ ID NO: 1)
Bb-12 ® (CHCC5445) nt #2710: - TCG CTG GGA TAC TTG AAC CAG AGT -
```

```
                                                        (SEQ ID NO: 2)
Bb12Tet-S139 (CHCC8902) nt #2710:   - TCG CTG GGA TAC TGA ACC AGA GTT -

(SEQ ID NO: 34)
Amino acid sequence:                - Ser Leu Gly Tyr opal (stop codon).
```

The illustration above shows a partial sequence of the tetW gene in CHCC5445. The underlined thymidine residue in Bb-12® (nt: 2722 in the tetW sequence) is deleted in the frameshift mutant, Bb12Tet-S139, resulting in an opal stop/nonsense codon 170 amino acids short of the wild type tetW gene product.

[nt #2722 has the nt position number #1405 in the sequence of tetW in table 2, SEQ ID 22].

DNA sequencing of the tetW gene from the other tetracycline sensitive isolate DR10TetS9X, a derivative of strain HN019 (CHCC7158), demonstrated a transition of a cytidine to a thymidine residue at nucleotide position #174, thus immediately generating an amber translational stop codon as depicted below and in Table 2.

```
                                                        (SEQ ID NO: 35)
Amino acid sequence:                - Gln Ser Val Val Gln Ser Val Arg -

(SEQ ID NO: 4)
DR10 ™ (HN019, CHCC7158) nt #2729:  -CAG AGC GTG GTT CAG TCT GTT CGG- (SEQ ID NO: 5)
DR10Tet-S9X (CHCC9070) nt #2729:    -CAG AGC GTG GTT TAG TCT GTT CGG- (SEQ ID NO: 36)
Amino acid sequence:                - Gln Ser Val Val amber (stop codon).
```

The illustration above shows a partial sequence of the tetW gene in CHCC7158, which is identical to the tetW gene in CHCC5445. The underlined cytidine residue in HN019 (nt: 1741) is substituted with a thymidine residue in the mutant strain, resulting in an amber stop/nonsense codon 498 amino acids short of the wild type tetW gene product. [nt #1741 has the nt position number #424 in DNA sequence of tetW in table 2, SEQ ID 22].

Example 4

Genetic Stability of the Tetracycline Sensitive Isolates Bb12Tet-S139 (CHCC8902), DR10Tet-S9X (CHCC9070) and Bb12Tet-S180

Determination of Back Mutation Rates by Cell Plating on MRS Agar with Tetracycline One ml of a culture of the Bb12Tet-S139 mutant strain ($1.6 \times 10^{-9}$ cells/ml) grown overnight was spread with 50 µl each onto 20 Petri dishes (diameter: 13.8 cm) with MRS agar supplied with tetracycline (15 µg/ml). After 24 hours of anaerobic incubation at 37° C., no colonies could be detected on the plates demonstrating that the reversion rate is less than $1.6 \times 10^{-9}$.

The same stability testing was performed for the DR10Tet-S9X strain. An over night culture of this strain ($1.1 \times 10^{-9}$ cells/ml) was likewise spread with 50 µl each onto 20 Petri dishes with MRS agar supplied with tetracycline (15 µg/ml). After the incubation period, 19 tetracycline resistant colonies were detected. The reversion rate for the amber mutation was calculated to $1.8 \times 10^{-8}$.

The reversion rate for the Bb12Tet-S180 strain was calculated to $1.7 \times 10^{-7}$.

Example 5

Physiological and Phenotypic Testings of the Two Tetracycline Sensitive Strains, Bb12Tet-S139 (CHCC8902) and DR10Tet-S9X (CHCC9070)

Growth Conditions of the Mutant Strains in MRS Broth.

Growth of the Bb12Tet-S139 and DR10Tet-S9X was compared (in triplicates) to their mother strains, CHCC5445 and CHCC7158, respectively, grown under similar conditions in MRS broth (200 ml with Cysteine-HCl) over a period of 24 hours. Samples for measuring the optical density at 600 nm was monitored all along the incubation period. The growth rates for both mutants were similar to those of the parent wild type strains indicating that the mutagenic treatment of the tetracycline sensitive isolates did not seem to hamper genes in their fermentative pathways.

Acidification Rates of the Two tetW Mutants.

The acidification (MRS broth), i.e. the conversion of pyruvate to lactic acid, was monitored (in duplicates) over a period of 6 hours and compared to the respective mother strains grown under the same conditions. No obvious difference in the rate of acidification was observed between the mutant derivatives of CHCC5445 and CHCC7158 and their mother strains.

DNA-Fingerprinting Analysis.

Pulsed-field gel-electrophoresis of the genomic SpeI- and XbaI-digested DNA from the two mutant tetW strains was performed according to standard methods (Hung and Bandziulis, 1990), and did not reveal any rearrangement of the SpeI- or XbaI-digested chromosomal pattern when compared to the respective wild type strains. This adds evidence to an overall isogenic background of the mutants and the mother strains.

Example 6

Genome Wide Gene Expression (Transcriptomic) Analysis Shows that the Gene-Expression of Bb12Tet-S139 is Indistinguishable from Bb-12®

Materials & Methods

Design and Production of Whole Genome Microarrays for Bb12

We have previously sequenced and set up whole genome microarrays for Bb12® (Garrigues et al. 2005). Briefly, Bb-12® was shotgun sequenced, resulting in 56 contigs.

Through further assembly analysis, it was clear that only a couple of percent of the sequence was missing. Within the almost 2.0 Mb genome sequence, 1612 putative CDSs (coding sequences) were identified. A specific 65-75mer oligo was designed for each gene with a few exceptions, such as very small putative genes. For a couple of genes, several oligos were designed. In all, 1569 oligos were designed from the sequence. In addition more than 100 control oligos were designed. Oligos were printed on UltraGAPS slides (Corning B. V., Schiphol-Rijk, The Netherlands) in four replicate copies as described previously (Pedersen et al. 2005).

RNA samples were collected in RNAprotect (QIAGEN, Valencia, Calif., USA) to stabilize the expression profile and total RNA was isolated (RNeasy, QIAGEN). 10 µg of RNA was copied into cDNA using the CyScribe Post-Labelling Kit with 1.65 µg of random nonamer as primer (Amersham Biosciences, Hillerød, Denmark). The test condition was labeled with Cy5 and the reference condition with Cy3. The two samples were pooled, and half of this was hybridized to the array. Instead of the 50% formamide recommended in the protocol, 60% was used (these conditions were established previously using the control oligos). After around 18 h of hybridization, the array was washed (Corning B.V.), scanned, and pre-analyzed as described previously (Pedersen et al. 2005). The array data was imported into Acuity 4.0 (Axon Instruments Inc., Union City, Calif., USA) where it was LOWESS normalized. A dataset was created with all identified spots. Data from oligos where only 0, 1, or 2 of the 4 replicate spots had been identified were removed. Similarly, data from oligos where the standard deviation between the normalized log 2(ratio)s was >0.5 were removed.

Results

The gene expression of Bb12Tet-139S was compared to that of Bb12 using the whole genome microarrays. Stationary cultures of both strains were inoculated at 1% (OD600=0.06) into fresh MRS+0.05% cysteine.HCl preheated at 37° C. OD600 was then measured every 30 min. In the OD range of 0.1-1.0AU (absorbing units), growth was exponential. The specific growth rate, µ, was 0.50 h$^{-1}$ (R2=0.9977) and 0.51 h$^{-1}$ (R2=0.9953) for Bb-12® and Bb12Tet-S139, respectively. Hence, there is no significant difference between the growth rates of the two strains. From RNA samples at OD=1.0AU (after six and half hours of growth) microarrays were produced. Bb12Tet-S139 and Bb-12® were the test and reference conditions, respectively. Of the 1569 genes represented on the microarray significant regulatory, data was obtained from 1271 genes.

As a rule of thumb, a gene is often considered to be differentially expressed if it is >2-fold up or down-regulated between two conditions (see for example Pedersen et al. 2005). None of the 1271 genes in the dataset were more than >2-fold differentially expressed. In comparison, when Bb12 was exposed to 0.1% bile salt, 86 and 123 genes were >2-fold up and down-regulated, respectively (Garrigues et al. 2005). Among these genes, 17 and 27 were even >4-fold up and down-regulated, respectively. This shows that if cell metabolism is perturbed, dramatic changes may occur with regards to gene expression. Similarly, when 1% of fructooligosaccharide (FOS) was added to the medium, only 2 genes were >2-fold differentially expressed. These 2 genes encode proteins involved in FOS utilization and were 5-fold up-regulated (Garrigues et al. 2005). This latter experiment shows that the growth conditions can be reproduced and that perturbations affecting particular parts of the metabolism can be identified. By combing the above results, it is clear that with regards to gene expression and general physiological state no adverse effects are observed in Bb12Tet-S139 compared to Bb-12®. Based on this, it can be assumed that Bb12Tet-S139 behaves as Bb-12® except for the sensitivity to tetracycline.

Example 7

Quantitative Mutant Specific Detection of Bb-12Tet-S139

In order to obtain a method for quantitative detection of BB-12TET-S139, a real-time PCR assay with a dual labeled probe was designed. The target for the assay is the tetW gene, more specifically the deletion site is targeted by the dual labeled probe.

Primers and Probe

The primers were designed with the help of the publicly available program "Primer 3". The probe was designed manually. LNA (locked nucleic acid, a proprietary technology owned by Exiqon, Vedbæk, Denmark) derivatives were incorporated into the probe in order to be able to shorten the probe and thereby obtain higher specificity. The annealing temperature, secondary structure and primer/probe hybridization were assessed with the help of Exiqon's programs. Primers were obtained from TAGC, Copenhagen, DK, the dual labeled probe was obtained from Exiqon, Vedbæk, DK.

Real Time PCR Reaction

The PCR reaction was run on the ABI 7500 (Applied Biosystems) under standard conditions: 15 s denaturation at 95° C., 1 min annealing and elongation at 60° C. for 40 cycles. The following reagents were used: TaqMan® Universal PCR Master Mix (2× concentrated), 300 nM forward primer and backward primer, 200 nM probe. The reaction volume was 25 µl.

Results

Assay Design

The assay design resulted in the following primers and probe: forward primer 5'-CAA TAC AAG AGC CGG GTT TC (SEQ ID NO: 23), backward primer 5'-GTG CTG ACC GGA CTG TAA TAA A-3' (SEQ ID NO: 24), probe 5'-FAM-AtActgaaccA-TAMRA-3' (SEQ ID NO: 25) (FAM=Carboxy-Fluorescein; TAMRA=Carboxy-Tetramethyl-rhodamin). Small letters in the probe sequence indicate LNA-derivatives. The size of the amplification product is 160 bp.

DNA Extraction

DNA was extracted from pure cultures with the help of the DNeasy Tissue Kit (Qiagen, Germany) following the instructions of the manufacturer for extraction from gram positive bacteria. DNA was extracted from fecal samples with the help of the QIAamp Stool DNA extraction Kit Qiagen, Germany) following the instructions for pathogen detection as described by the manufacturer.

Specificity Testing

The specificity of the assay was tested against the wild type, some *Bifidobacterium* reference strains (see table 8-1) and mouse and human fecal DNA.

The assay was fully specific for BB-12TET-S139, and no amplification above the threshold was observed for the wild-type or any of the other *Bifidobacterium* samples.

TABLE 8-1

List of reference strains used to verify the specific detection of Bb-12Tet-S139.

| CHCC | Strain | Species |
|---|---|---|
| 8918 | LMG11596 | Bifidobacterium gallicum |
| 9084 | ATCC25527 | Bifidobacterium animalis ssp. animalis |
| 9081 | DSM20219 | Bifidobacterium longum biovar. longum |
| 9078 | DSM20213 | Bifidobacterium breve |
| 9076 | ATCC29521 | Bifidobacterium bifidum |
| 9074 | ATCC15703 | Bifidobacterium adolescentis |
| 9080 | ATCC15697 | Bifidobacterium longum biovar. infantis |
| 4266 | ATCC27535 | Bifidobacterium angulatum |
| 8912 | LMG10505 | Bifidobacterium pseudocatenulatum |
| 2182 | Bb46 | Bifidobacterium longum biovar. longum |
| 8914 | LMG11045 | Bifidobacterium dentium |
| 8916 | LMG21589 | Bifidobacterium scardovii |
| 5445 | Bb-12 ® | Bifidobacterium animalis ssp. lactis |

Conclusion

Thus, this assay can be used to identify *Bifidobacterium animalis* ssp. *lactis* strain BB-12TET-S139.

Example 8

Production and Stability of Freeze-Dried Cultures

An examination of the formulated, freezedried strains' ability to survive at 30° C. for 3 weeks at 2 different oxygen and humidity levels was performed.

Materials:

Bb-12® (DSM15954); 2 freeze-dried bulks and one blend Bb-12Tet-S139 (DSM17281). 2 freezedried bulks and one blend. In total 6 samples are used for the study. The freeze-dried bulks are produced according to standard recipe. Blends are grinded, freeze-dried bulk mixed with dextrose with a water activity below 0.15.

Methods:

Each sample is divided into 3 portions, which are treated as indicated in table 9-1 for 3 weeks.

TABLE 9-1

Conditions for stability testing of freeze-dried cultures.

|  | Reference | Treatment 1 | Treatment 2 |
|---|---|---|---|
| Temperature Conditions during the test period | −50 ± 5° C. Kept in sealed alu-bag | +30° C. ± 2° C. Kept in sealed alu-bag | +30° C. ± 2° C. Kept in an open container in a climate chamber approx 15% rH |

After the test period, a CFU/g analysis is performed twice on all samples.

CFU/q

A known amount of sample is homogenized with diluent, and decimal dilutions are prepared. Appropriate dilutions are mixed with MRS Agar from OXOID added 0.05% cystein-hydrochloride, then incubated for 3 days at 37° C. in an anaerobic chamber using AnaerGen™ from OXOID. At least 4 petridishes with 30 to 300 colonies are used for the enumeration.

Survival:

The survival is calculated as follows:

Survival %: (Log CFU/g in sample after treatment*100)/(Log CFU/g in reference sample).

Results:

Are shown in table 9-2 below.

TABLE 9-2

Survival of freeze-dried cultures (%)

|  | Treatment 1 | | Treatment 2 | |
|---|---|---|---|---|
|  | Bb-12Tet-S139 | Bb-12 ® | Bb-12Tet-S139 | Bb-12 ® |
| Freeze-dried bulk |  |  |  |  |
| 1 |  | 99% |  | — |
| 2 | 100% |  | 99% |  |
| 3 |  | 100% |  | 98% |
| 4 | 99% |  | 98% |  |
| Blends |  |  |  |  |
| A |  | 100% |  | 97% |
| B | 99% |  | 97% |  |

Conclusion:

There is no difference between Bb-12® and Bb-12Tet-S139 regarding their survival for 3 weeks at +30° C. or their survival in sealed alu-bags at +30° C. and approx. 15% rH. This is true both for pure freeze-dried cultures as well as for cultures mixed with excipients (blends).

Example 9

Survival in Artificial Gastric Juice

The survival of a probiotic bacterium through the human gastrointestinal tract is considered to be an important factor for its probiotic functionality.

*Bifidobacterium animalis* subsp. *lactis* strain Bb-12® has an excellent tolerance to gastric juice and bile salt. The in vitro test used for acid tolerance is based on the measurement of surviving bacteria after their exposure an artificial gastric juice.

*Bifidobacterium animalis* subsp. *lactis* Bb-12Tet-S139, cultured under anaerobic conditions overnight in MRS (Difco) at 37° C., was tested for its tolerance to the artificial gastric juice compared to BB-12.

The gastric juice was made by mixing 2.0 g of sodium chloride (Merck 1.06404.1000) and 3.2 g and pepsin powder (Sigma P-7000) in water. Then 80 ml of 1 M hydrochloric acid was added and the mixture diluted to 1000 ml with $H_2O$. Final adjustment to pH=2 was done with 5 M NaOH. The overnight bacterial culture was washed three times with 0.9% saline diluent supplemented with 1.5% tryptone at pH=7, and then added to the gastric juice followed by sampling at different time intervals.

The survival rate of the cells from each sample was assayed by plating the cells on MRS agar supplemented with 0.05% Cystein HCl and determining the number of colony forming units (c.f.u). The cells were exposed to the gastric juice (pH=2) at 37° C. up to 90 min. The dataset (see table $10^{-1}$) was analysed by the Mann-Whitney U-test.

TABLE 10-1

Survival in artificial gastric juice (%). Average of three experiments

| Sample (1 min 100%) | % Survival 30 min | Standard Deviation | % Survival 60 min | Standard Deviation | % Survival 90 min | Standard deviation |
|---|---|---|---|---|---|---|
| BB-12 ® | 103.2 | 7.10 | 104.5 | 7.6 | 98.1 | 7.9 |
| Bb-12Tet-S139 | 107.4 | 3.2 | 102.5 | 9.4 | 103.5 | 12.6 |

Conclusion

No significant difference was found between BB-12® and Bb-12Tet-S139 in relation to gastric acid tolerance.

Example 10

Tolerance to Bile Acids

The survival of any potential probiotic bacterium through the human gastrointestinal tract is considered to be important for its probiotic functionality. *Bifidobacterium animalis* subsp. *lactis* strain Bb-12® has an excellent resistance to bile salt.

In the present experiment, the *Bifidobacterium animalis* subsp. *lactis* strain Bb-12Tet-S139 was tested for its resistance to bovine and porcine bile extracts compared to Bb-12®.

Tolerance towards bile was assayed by plating cells on agar plates supplemented with bile salt of varying concentrations essentially as described by Noriega L. et. al. Int. J. Food Microbiol 94, 79-86, 2004. Minimum inhibitory concentration (MIC) determinations of both strains were made on MRS-Cystein HCl agar plates supplemented with two-fold serial dilutions of bovine bile (Sigma B3883) and porcine bile extract (Sigma B8631) in concentrations from 2% to 0.062% w/v.

Results

Both strains were shown to be tolerant to bile salt concentrations up to at least 2%.

Experiments were carried out in triplicate. Results are shown in table 11-1.

TABLE 11-1

Tolerance to bile acids. Bacterial growth on MRS-Cystein HCl agar plates supplemented with 2% w/v bile salts.

| | Bovine bile | Porcine bile extract |
|---|---|---|
| Bb-12 ® (A) | + | + |
| Bb-12 ® (B) | + | + |
| Bb-12 ® (C) | + | + |
| Bb-12Tet-S139 (A) | + | + |
| Bb-12Tet-S139 (B) | + | + |
| Bb-12Tet-S139 (C) | + | + |

+ indicates clear bacterial growth on all agar plates

Conclusion

Both Bb-12® and Bb-12Tet-S139 are tolerant to at least 2% bile acids, indicating a minimum inhibitory concentration that is higher than 2% for both strains. Tolerance to bile salts is indicative of adaptation to the conditions in the gastrointestinal tract.

Example 11

Three New Tetracycline-Sensitive Derivatives of Two Probiotic Strains of *Bifidobacterium animalis* subspecies *lactis*—their Isolation and Molecular Characterization The three new derivatives were cultured, mutated, selected and characterized as described in Example 1, 2 and 3.

Bb-12Tet-S79 and Bb-12Tet-S180 are derivatives of *Bifidobacterium animalis* subspecies *lactis* Bb-12®. DR10Tet-S33 is a derivative of HN019 (DR10™).

Bb-12Tet-S180,

DNA sequencing of the tetW gene from the tetracycline sensitive isolate Bb-12Tet-S180, a derivative of *Bifidobacterium animalis* subspecies *lactis* Bb-12® (CHCC5445), demonstrated a transversion of an adenine to a cytidine residue at nucleotide position #2731 in Tab. 2 (SEQ ID 22) generating an amino acid substitution from a Serine to an Arginine as depicted below.

```
                                                      (SEQ ID NO: 38)
Amino acid sequence:       - Tyr Leu Asn Gln Ser Phe Gln Asn (SEQ ID NO: 37)
Bb-12 (CHCC5445) nt #2719  - TAC TTG AAC CAG AGT TTT CAA AAC (SEQ ID NO: 26)
Bb-12Tet-S180 nt #2719     - TAC TTG AAC CAG CGT TTT CAA AAC (SEQ ID NO: 39)
Amino acid sequence:         Tyr Leu Asn Gln Arg Phe Gln Asn
```

The above sequence show a partial amino acid sequence of the tetW gene found in CHCC5445. The underlined adenine residue in CHCC5445 (nt: 2731) is substituted with a cytidine residue in the mutant strain, resulting in an amino acid substitution 168 amino acids before the translational stop codon.

Multiple Mutants DR10tet-S33 and Bb-12Tet-S79,

DNA sequencing of the tetW genes from the tetracycline sensitive isolates DR10Tet-S33 and Bb-12Tet-S79 demonstrated two and three nucleotide substitutions, respectively, each of which gave rise to an amino acid substitution in the tetW gene product as described below.

DR10tet-S33, nt #1546[G] to 1546[T] in the triplet GGC to TGC resulted in an amino acid substitution of Glycine to Cysteine.

nt #1774[A] to 1774[G] in the triplet ATC to GTC resulted in an amino acid substitution of Isoleucine to Valine. See Tab. 2 (SEQ ID 22).

Bb-12Tet-S79, nt #1358[C] to 1358[A] in the triplet GCT to GAT resulted in an amino acid substitution of Alanine to Aspartic acid.

nt #3023[A] to 3023[G] in the triplet CAG to CGG resulted in an amino acid substitution of Glutamine to Arginine.

nt #3095[T] to 3095[C] in the triplet CTG to CCG resulted in an amino acid substitution of Leucine to Proline. See Tab. 2 (SEQ ID 22).

Sensitivity,

The tet-sensitive isolates were subjected to E-test susceptibility screening according to the methods described by M. Danielsen and A. Wind (2003), to determine their tetracycline sensitive threshold. The result is summarized in table 12-1 below:

TABLE 12-1

Minimum inhibitory concentrations (MICs) of tetracycline of probiotic strains of *Bifidobacterium animalis* subspecies *lactis* and two derivatives thereof.

| Type | strain | tet-susceptibility according to the E-test (MIC value) |
| --- | --- | --- |
| parent strain | *Bifidobacterium animalis* subspecies *lactis* Bb-12 ® | ≧16 µg/ml |
| mutant strain | Bb-12Tet-S79 | ≦1.0 µg/ml |
| mutant strain | Bb12Tet-S139 | ≦1.0 µg/ml |
| mutant strain | Bb-12Tet-S180 | ≦1.0 µg/ml |
| parent strain | *Bifidobacterium animalis* subspecies *lactis* HN019 (DR10 ™). | ≧16 µg/ml |
| mutant strain | DR10Tet-S9X | ≦1.0 µg/ml |
| mutant strain | DR10Tet-S33 | ≦1.0 µg/ml |

Example 12

Classification of Tetracycline-Sensitive Variants of Two Probiotic Strains of *Bifidobacterium animalis* Subspecies *lactis*

As mentioned in Example 2, approximately 85% of the putative "tetracycline sensitive" isolates managed to grow in liquid MRS broth containing tetracycline (10 µg/ml) under these conditions. The remaining 15% tetracycline sensitive isolates were then subjected to E-test susceptibility screening according to the methods described by M. Danielsen and A. Wind (2003), to determine their tetracycline sensitive threshold.

In general, the E-test revealed two classes of tetracycline sensitive mutants:

Class 1: Growth at tetracycline conc. of 1.5 µg/ml or less according to the E-test; and Class 2: Growth at tetracycline concentrations >1.5 µg/ml;

The tetW gene was analysed in a representative number of Class 1 and Class 2 tetracycline sensitive mutants.

The result being:

Class 1: Growth at tetracycline conc. ≦1.5 µg/ml; are tetracycline sensitive mutants that are characterized in having nucleotide (nt) deletions or nt substitutions, some of which resulting in the introduction of stop codons in the open reading frame of the tetW gene, and Class 2: Growth at tetracycline concentrations >1.5 µg/ml; no mutations in tetW. This class of mutations is most probably caused by mutations in cell walls or transport proteins.

Conclusion

Until now, all mutations that are characterized by an E-test value ≦1.5 µg tet/ml contained a mutated tetW. This opens for a selection procedure, which results in the selection of tetracycline-sensitive Bifidobacteria which, with a high probability, contains an inactivated tetW gene.

Example 13

Three Additional Tetracycline-Sensitive Derivatives of a Probiotic Strain of *Bifidobacterium animalis* Subspecies *lactis*—their Isolation and Molecular Characterization The three new derivatives were cultured, mutated, selected and characterized as described in Example 1, 2 and 3.

Bb-12tetW-S73, Bb-12tetW-S14 and Bb-12tetW-S4 are derivatives of *Bifidobacterium animalis* subspecies *lactis* Bb-12®.

Bb-12tetW-S73,

DNA sequencing of the tetW gene from the tetracycline sensitive isolate Bb-12tetW-S73, a derivative of *Bifidobacterium animalis* subspecies *lactis* Bb-12® (CHCC5445), demonstrated a change of a thymine to a guanine residue at nucleotide position #1573 in Tab. 2 (SEQ ID 22) (TAC>GAC) generating an amino acid substitution from a Tyrosine to an Aspartic Acid.

Bb-12tetW-S14,

DNA sequencing of the tetW gene from the tetracycline sensitive isolate Bb-12tetW-S14, a derivative of *Bifidobacterium animalis* subspecies *lactis* Bb-12® (CHCC5445), demonstrated a change of a thymine to a cytosine residue at nucleotide position #2869 in Tab. 2 (SEQ ID 22) (TCA>CCA) generating an amino acid substitution from a Serine to an Proline.

Bb-12tetW-S4,

DNA sequencing of the tetW gene from the tetracycline sensitive isolate Bb-12tetW-S4, a derivative of *Bifidobacterium animalis* subspecies *lactis* Bb-12® (CHCC5445), demonstrated a change of an adenine to a guanine residue at nucleotide position #3176 in Tab. 2 (SEQ ID 22) (CAG>CGG) generating an amino acid substitution from a Glutamine to an Arginine.

Sensitivity,

The tet-sensitive isolates were subjected to E-test susceptibility screening according to the methods described by M. Danielsen and A. Wind (2003), to determine their tetracycline sensitive threshold. The result is summarized in table 13-1 below:

TABLE 13-1

Minimum inhibitory concentrations (MICs) of tetracycline Bb-12 and 3 new derivatives thereof.

| type | strain | tet-susceptibility according to the E-test (MIC value) |
| --- | --- | --- |
| parent strain | *Bifidobacterium animalis* subspecies *lactis* Bb-12 ® | ≧16 µg/ml |
| mutant strain | Bb-12tetW-S73 | ≦1.0 µg/ml |
| mutant strain | Bb-12tetW-S14 | ≦1.0 µg/ml |
| mutant strain | Bb-12tetW-S4 | ≦1.0 µg/ml |

Barbosa, T. M., K. P. Scott, and H. J. Flint. 1999. Evidence for recent intergeneric transfer of a new tetracycline resistance gene, tet(W), isolated from *Butyrivibrio fibrisolvens*, and the occurrence of tet(O) in ruminal bacteria. Environ. Microbiol. 1:53-64.

Billington, S. J. J. G. Songer, and B. H. Jost (2002) Widespread Distribution of a Tet W Determinant among Tetracycline-Resistant Isolates of the Animal Pathogen *Arcano-*

*bacterium pyogenes*. ANTIMICROBIAL AGENTS AND CHEMOTHERAPY, 46:1281-1287.

Cai et al (2000) MicrobioL ImmunoL 44, 815-820

Chopra, I., and M. Roberts (2001). Tetracycline antibiotics: mode of action applications, molecular biology, and epidemiology of bacterial resistance". Microbiol. Mol. Biol. Rev. 65:232-260.

Chopra, I., and M. Roberts. 2001. Tetracycline antibiotics: mode of action, applications, molecular biology, and epidemiology of bacterial resistance. Microbiol. Mol. Biol. Rev. 65:232-260.

de Man, J. C., M. Rogosa, and M. E. Sharpe. 1960. A medium for the cultivation of lactobacilli. J. Appl. Bacteriol. 23:130-135.

EFSA (2005) Opinion of the Scientific Panel on Additives and Products or Substances used in Animal Feed on the updating of the criteria used in the assessment of bacteria for resistance to antibiotics of human or veterinary importance (Question N° EFSA-Q-2004-079) The EFSA Journal 223, 1-12.

Garrigues, C., B. Stuer-Lauridsen and E. Johansen (2005). Characterisation of *Bifidobacterium animalis* subsp. *lactis* BB-12 and other probiotic bacteria using genomics, transcriptomics and proteomics. Aust. J. Dairy Tech. 60: 84-92.

Hung, L. and R. Bandziulis, Promega Notes 24: 1-2, 1990, Promega, Madison, Wis. Lachman, L. et al (Ed.) 1986. The Theory and Practice of Industrial Pharmacy. Third Edition. Lea & Febiger, Philadelphia.

List no. 62 (1997) Int. J. Syst. Bacteriol 47, 915-916

M. A. Innis and D. H. Gelfand (1990) Optimization of PCRs, p. 3-12. In M. A. Innis, D. H. Gelfand, J. J. Sninsky, and T. J. White (ed), PCR protocols, a guide to methods and applications. Academic Press, San Diego, Calif.

M. Danielsen and A. Wind. 2003 "Susceptibility of *Lactobacillus* spp. to antimicrobial agents". Int. J. Food Microbiol. 82:1-11.

Masco et al (2004) Int. J. Syst. EvoL MicrobiaL 54, 1137-1143

Meile et al (1997) System. AppL MicrobioL 20, 57-64

Miller, J. H. (1972) "Experiments in molecular genetics", p 230-234. Cold Spring Harbor Laboratory, Cold Spring Harbor, N.Y.

Minutes (2001) Int. J. Syst. EvoL MicrobioL 51, 259-261

Moubareck, C. et al. (2005) Antimicrobial susceptibility of Bifidobacteria. J. Antimicrobial Chemotherapy 55: 38-44.

Pedersen, M. B., Iversen, S. L., Sørensen, K. I., and E. Johansen. 2005. The long and winding road from the research laboratory to industrial applications of lactic acid bacteria. FEMS Microbiology Reviews, accepted.

Scott, K. P., C. M. Melville, T. M. Barbosa, and H. J. Flint (2000) Occurrence of the New Tetracycline Resistance Gene tet(W) in Bacteria from the Human Gut. ANTIMICROBIAL AGENTS AND CHEMOTHERAPY, 44: 775-777.

Silliker, J. H. et al (Ed.) 1980. pH and acidity. IN: Microbial Ecology of Foods, vol. 1 pp. 92-111. Academic Press, New York.

Silva, A.M., Bambirra, E. A., Oliveira, A. L., Souza, P. P., Gomes, D. A., Vieira, E. C., Nicoli, J. R. (1999) Protective effect of bifidus milk on the experimental infection with *Salmonella enteritidis* subsp. *typhimurium* in conventional and gnotobiotic mice. Journal of Applied Microbiology, 86: 331-336.

WO 97/16198, (Chr. Hansen AIS Biosystems), 9 May 1997

Yazid, A. M., A. M. Ali, M. Shuhaimi, V. Kalaivaani, M. Y. Rokiah and A. Reezal (2000) Antimicrobial susceptibility of bifidobacteria. Letters in Applied Microbiology 2000, 31, 57-62

Zhou, J. S., C. J. PillidgeC, P. K. Gopal and H. S. Gill (2005) Antibiotic susceptibility profiles of new probiotic Lactobacillus and *Bifidobacterium* strains. International Journal of Food Microbiology 98:211-217.

Regarding Deposited Microbial Organisms [Expert Solution]

For all deposited microbial organisms mentioned in the present patent application the following applies.

In respect to those designations in which a European Patent is sought a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies. (Rule 28 (4) and 28 (5) EPC).

| Applicant's or agent's file reference 40731PC01 | International application No. PCT/DK2006/050020 |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 16, line 33.

B. IDENTIFICATION OF DEPOSIT — Further deposits are identified on an additional sheet ☐

Name of depositary institution
DSMZ-Deutche Sammlung vor Mikroorganismen und Zellkulturen GmbH Address of depositary institution (including postal code and country)
Mascheroder Weg 1b
D-38124 Brausnweig
Germany

| Date of deposit | Accession Number |
|---|---|
| 17 May 2005 | DSM 17280 |

C. ADDITIONAL INDICATIONS (leave blank if not applicable)  This information is continued on an additional sheet ☒

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
☐ This sheet was received with the international application
Authorized officer For International Bureau use only
☐ This sheet was received by the International Bureau on:
Authorized officer Indications Relating To Deposited Microorganisms
(PCT Rule 12bis)

Additional Sheet

In addition to the microorganism indicated on page 16 of the description, the following microorganisms have been deposited with
DSM-Deutsche Sammlung von Mikroorganismen und Cellkulturen GmbH MascheroderWeg 1b, D-38124 Braunschweig, Germany
on the dates and under the accession numbers as stated below:

| Accession number | Date of deposit | Description Page No. | Description Line No. |
|---|---|---|---|
| DSM 17281 | 17 May 2005 | 22 | 32 |
| DSM 17282 | 17 May 2005 | 23 | 13 |
| DSM 15954 | 13 Oct. 2003 | 30 | 20 |

For all of the above-identified deposited microorganisms, the following additional indications apply:
As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

TABLE 1

Oligonucleotides used for PCR analyses and DNA sequencing of the tetracycline resistance-encoding tetW gene of Bb-12.
(SEQ ID NOS 7-21, respectively, in order of appearance).

| Primer | Sequence (5' to 3') | Nucleotide positions* |
|---|---|---|
| Stps.D5 | GAGCATCGCTTAATTCCTTCGAGGGG | -394 : -369 |
| StetW.D | CGAGGGGACTTTGGCCCACCGCTGGGTGG | -375 : -347 |
| StetW.D1 | GCAGGCAGGCACGTCCATCCGCCTC | -199 : -175 |
| Stps.R3 | GGCTTCTGCCACCGTGGCCTCGTCAC | 234 : 209 |
| tpsW.R1 | CCTGTCCTTGTCCACGCCGATATGCGC | 554 : 526 |
| tetWx.D1 | CGGCACCTGCTGTATAATGCGGATTGTGGC | 1022 : 1051 |
| tetW.Dup | GTGGGAACAAAGGATTATGATAGTCCC | 1092 : 1118 |
| tetWx.D4 | GGCTGGCGTTGATTTGCAGAGCGTGG | 1713 : 1738 |
| tetW.D500 | GCAGACGGTGTCGCTGTCCCCGG | 1782 : 1804 |
| tetWx.R2 | CCGGGGACAGCGACACCGTCTGC | 1804 : 1782 |
| tetWx.D3 | GGAGCGGCCGCTCAAAGCAGCCAGCC | 2580 : 2625 |
| tetWx.R3 | GGCTGGCTGCTTTGAGCGGCCGCTCC | 2625 : 2580 |
| tetWx.R5 | GCCCAAAAACGGGTTGGGCGGCACCTCG | 2645 : 2619 |
| tetW.R500 | CCAGCCCGTAACGGATACCATCCC | 2773 : 2750 |
| tetWx.R4 | GATGGTCGCATGATCGGCGGGGTCACTCC | +262 : +233 |

*Numbering is based on the DNA sequence illustrated in table 2. The prefix "D" indicates a direct primer derived from the sense strand. The prefix "R" indicates a reverse primer complementary to the sense strand.

TABLE 2

The tetW DNA sequence flanked by the upstream transposase gene, tps, from *Bifidobacterium animalis* Bb-12 (SEQ ID NO: 22).
and the complement disclosed as SEQ ID NO: 42).
Transposase and Tetracycline sequences as SEQ ID NOS 40-41, respectively.

```
1   ORF encoding a Transposase
    CAGATGACGATTTCCGCATTCAGCGACGAACTGGCACAGGTGCGGACGAAGAAAAAGCA
    -----------------------------------------------------------  60
    GTCTACTGCTAAAGGCGTAAGTCGCTGCTTGACCGTGTCCACGCCTGCTTCTTTTTCGT
        M   T   I   L   A   F   S   D   E   L   A   Q   V   R   T   K   K   K   A TTTCTCGACCAGATTGAACGGATCGTCCCGTGGAAGGAATGGCTTGCCATGATTCAGCCG
    -----------------------------------------------------------  120
    AAAGAGCTGGTCTAACTTGCCTAGCAGGGCACCTTCCTTACCGAACGGTACTAAGTCGGC
     F   L   D   Q   I   E   R   I   V   P   W   K   E   W   L   A   M   I   Q   P TGCTATTACAAAGGAGAGCGCGGCAACAAACCCTATCCGCTGGAGATCATGCTCCGACTG
    -----------------------------------------------------------  180
    ACGATAATGTTTCCTCTCGCGCCGTTGTTTGGGATAGGCGACCTCTAGTACGAGGCTGAC
     C   Y   Y   K   G   E   R   G   N   K   P   Y   P   L   E   I   M   L   R   L TATCTGCTGCAAAACCTCTATGACCTGAGTGACGAGGCCACGGTGGCAGAAGCCATCGAC
    -----------------------------------------------------------  240
```

TABLE 2-continued

The tetW DNA sequence flanked by the upstream transposase gene,
tps, from *Bifidobacterium animalis* Bb-12 (SEQ ID NO: 22).
and the complement disclosed as SEQ ID NO: 42).
Transposase and Tetracycline sequences as SEQ ID NOS 40-41,
respectively.

```
ATAGACGACGTTTTGGAGATACTGGACTCACTGCTCCGGTGCCACCGTCTTCGGTAGCTG
 Y  L  L  Q  N  L  Y  D  L  S  D  E  A  T  V  A  E  A  I  D

AGCCGCGCATTTTCGGAGTTCTGCGGCGTCGATTCCAGCAACCAGGTTCCGAACGGGGAT
------------------------------------------------------------   300
TCGGCGCGTAAAAGCCTCAAGACGCCGCAGCTAAGGTCGTTGGTCCAAGGCTTGCCCCTA
 S  R  A  F  S  E  F  C  G  V  D  S  S  N  Q  V  P  N  G  D

ACTCTTGGCCGGTTCCGGAACTTGCTGATCAAGAACGGACTGCAGGAGAAGCTGTTCGCT
------------------------------------------------------------   360
TGAGAACCGGCCAAGGCCTTGAACGACTAGTTCTTGCCTGACGTCCTCTTCGACAAGCGA
 T  L  G  R  F  R  N  L  L  I  K  N  G  L  Q  E  K  L  F  A

CAGGTGGTAGCAGCGCTCATGGAACGTGGCCTCATTCTGAAAAAGGGCACCATTGTAGAT
------------------------------------------------------------   420
GTCCACCATCGTCGCGAGTACCTTGCACCGGAGTAAGACTTTTTCCCGTGGTAACATCTA
 Q  V  V  A  A  L  M  E  R  G  L  I  L  K  K  G  T  I  V  D

TCCACCATCATTTCCGCCCCTCTTCTACCAAGAATAAGGAAAAGAAACGGGATCCGGAT
------------------------------------------------------------   480
AGGTGGTAGTAAAGGCGGGGGAGAAGATGGTTCTTATTCCTTTTCTTTGCCCTAGGCCTA
 S  T  I  I  S  A  P  S  S  T  K  N  K  E  K  K  R  D  P  D

GCCCACCAAGTCAAGAAGGGCAACACCTGGCACTTTGGGTACAAAGCGCATATCGGCGTG
------------------------------------------------------------   540
CGGGTGGTTCAGTTCTTCCCGTTGTGGACCGTGAAACCCATGTTTCGCGTATAGCCGCAC
 A  H  Q  V  K  K  G  N  T  W  H  F  G  Y  K  A  H  I  G  V

GACAAGGACAGCGGACTGGTTCACACAGTGGAAGCTACACCGGCAAATGTCCACGACGTT
------------------------------------------------------------   600
CTGTTCCTGTCGCCTGACCAAGTGTGTCACCTTCGATGTGGCCGTTTACAGGTGCTGCAA
 D  K  D  S  G  L  V  H  T  V  E  A  T  P  A  N  V  H  D  V

GCGGAAGTGCCGAAATTATTGACGGGAGAGGAAGAAACAGTCTATGGAGACAGCGGTTAT
------------------------------------------------------------   660
CGCCTTCACGGCTTTTTAACTGCCCTCTCCTTCTTTGTCAGATACCTCTGTCGCCTTATA
 A  E  V  P  K  L  L  T  G  E  E  E  T  V  Y  G  D  S  G  Y

CTCGGCGCAGGTAAGCGCGAAGATGCCGTAGTCCGAAACAAAGCTGGCCGGAAAATCAAG
------------------------------------------------------------   720
GAGCCGCGTCCATTCGCGCTTCTACGGCATCAGGCTTTGTTTCGACCGGCCTTTTAGTTC
 L  G  A  G  K  R  E  D  A  V  V  R  N  K  A  G  R  K  I  K

TACAAGATCAATCGTCGTCCATCGCAGATGAAGAAACTGAGCAAAAGCGGGCAGTACGCA
------------------------------------------------------------   780
ATGTTCTAGTTAGCAGCAGGTAGCGTCTACTTCTTTGACTCGTTTTCGCCCGTCATGCGT
 Y  K  I  N  R  R  P  S  Q  M  K  K  L  S  K  S  G  Q  Y  A

GCAAAGAAAGCGGAACGGGCGAAATCCTCAGTGCGAGCAAAAGTAGAGCATGTATTCGGT
------------------------------------------------------------   840
CGTTTCTTTCGCCTTGCCCGCTTTAGGAGTCACGCTCGTTTTCATCTCGTACATAAGCCA
 A  K  K  A  E  R  A  K  S  S  V  R  A  K  V  E  H  V  F  G

GTCGTTAAGAAGCAGCTGCGCTTCCGAAAAACGCGATACCGAGGGCTTGAAAAGGAACAA
------------------------------------------------------------   990
CAGCAATTCTTCGTCGACGCGAAGGCTTTTTGCGCTATGGCTCCCGAACTTTTCGTTGTT
 V  V  K  K  Q  L  R  F  R  K  T  R  Y  R  G  L  E  K  Q  Q

GCCAAATTCAATATCATGTTTGCGTTGGCAAATCTGATTCTGGCTGACAGACCCTGTCTG
------------------------------------------------------------   960
CGGTTTAAGTTATAGTACAAACGCAACCGTTTAGACTAAGACCGACTGTCTGGGACAGAC
 A  K  F  N  I  H  F  A  L  A  N  L  I  L  A  D  R  P  C  L

Transposase Stop
GCAGCTTGAGTCAGTGCGCCTTTGCGGACAAAAAATTCGGAGGTTATCCACAGTTTTTAT
------------------------------------------------------------  1020
CGTCGAACTCAGTCACGCGGAAACGCCTGTTTTTTAAGCCTCCAATAGGTGTCAAAAATA
 A  A  *

TCGGCACCTGCTGTATAATGCGGATTGTGGCATTTGTGCGGTGTTGCCTTAAATAAAACT
------------------------------------------------------------  1080
AGCCGTGGACGACATATTACGCCTAACACCGTAAACACGCCACAACGGAATTTATTTTGA

ATAATCAAATAGTGGGAACAAAGGATTATGATAGTCCCTTTTGTAGGGGCTTAGTTTTTT
```

TABLE 2-continued

The tetW DNA sequence flanked by the upstream transposase gene, tps, from *Bifidobacterium animalis* Bb-12 (SEQ ID NO: 22). and the complement disclosed as SEQ ID NO: 42). Transposase and Tetracycline sequences as SEQ ID NOS 40-41, respectively.

```
                                                              1140
TATTAGTTTATCACCCTTGTTTCCTAATACTATCAGGGAAAACATCCCCGAATCAAAAAA

GTACCCAATTTAAGAATACTTTTGCCTTATCAATTTTGACATATCCCCAAAAACAGCACT
                                                              1200
CATGGGTTAAATTCTTATGAAAACGGAATAGTTAAAACTGTATAGGGGTTTTTGTCGTGA

CACAAACAGGTGTATGCTGTATATGTGTATGTCCGCAAATTATCATCCCCAGTGGTAAAA
                                                              1260
GTGTTTGTCCACATACGACATATACACATACAGGCGTTTAATAGTAGGGGTCACCATTTT

Tetracycline Start
GTATTTTACTGCTGGGGATTTTTATGCCCTTCGGGGCAGTAAAGGGAGGACAATCACATG
                                                              1320
CATAAAATGACGACCCCTAAAAATACGGGAAGCCCCGTCATTTCCCTCCTGTTAGTGTAC
                                                             M AAAATAATCAATATTGGAATTCTTGCCCATGTAGACGCTGGAAAGACGACCTTGACGGAG
                                                              1380
TTTTATTAGTTATAACCTTAAGAACGGGTACATCTGCGACCTTTCTGCTGGAACTGCCTC
 K  I  I  N  I  G  I  L  A  H  V  D  A  G  K  T  T  L  T  E AGCCTGCTATATGCCAGCGGAGCCATTTCAGAACCGGGGAGCGTCGAAAAAGGGACAACG
                                                              1440
TCGGACGATATACGGTCGCCTCGGTAAAGTCTTGGCCCCTCGCAGCTTTTTCCCTGTTGC
 S  L  L  Y  A  S  G  A  I  S  E  P  G  S  V  E  K  G  T  T AGGACGGACACCATGCTTTTGGAGCGGCAGCGTGGGATTACCATTCAAGCGGCAGTCACT
                                                              1500
TCCTGCCTGTGGTACGAAAACCTCGCCGTCGCACCCTAATGGTAAGTTCGCCGTCAGTGA
 R  T  D  T  M  L  L  E  R  Q  R  G  I  T  I  Q  A  A  V  T TCCTTCCAGTGGCACAGATGTAAAGTCAACATTGTGGATACGCCCGGCCACATGGATTTT
                                                              1560
AGGAAGGTCACCGTGTCTACATTTCAGTTGTAACACCTATGCGGGCCGGTGTACCTAAAA
 S  F  Q  W  H  R  C  K  V  N  I  V  D  T  P  G  H  M  D  F TTGGCGGAGGTGTACCGCTCTTTGGCTGTTTTAGATGGGGCCATCTTGGTGATCTCCGCT
                                                              1620
AACCGCCTCCACATGGCGAGAAACCGACAAAATCTACCCCGGTAGAACCACTAGAGGCGA
 L  A  E  V  Y  R  S  L  A  V  L  D  G  A  I  L  V  I  S  A AAAGATGGCGTGCAGGCCCAGACCCGTATTCTGTTCCATGCCCTGCGGAAAATGAACATT
                                                              1680
TTTCTACCGCACGTCCGGGTCTGGGCATAAGACAAGGTACGGGACGCCTTTTACTTGTAA
 K  D  G  V  Q  A  Q  T  R  I  L  F  H  A  L  R  K  M  N  I CCCACCGTTATCTTTATCAACAAGATCGACCAGGCTGGCGTTGATTTGCAGAGCGTGGTT
                                                              1740
GGGTGGCAATAGAAATAGTTGTTCTAGCTGGTCCGACCGCAACTAAACGTCTCGCACCAA
 P  T  V  I  F  I  N  K  I  D  Q  A  G  V  D  L  Q  S  V  V nt #1741-C substituted to T in DR10Tet-S9x
CAGTCTGTTCGGGATAAGCTCTCCGCCGATATTATCATCAAGCAGACGGTGTCGCTGTCC
                                                              1800
GTCAGACAAGCCCTATTCGAGAGGCGGCTATAATAGTAGTTCGTCTGCCACAGCGACAGG
 Q  S  V  R  D  K  L  S  A  D  I  I  I  K  Q  T  V  S  L  S
 *  (amber)

CCGGAAATAGTCCTGGAGGAAAATACCGACATAGAAGCATGGGATGCGGTCATCGAAAAT
                                                              1860
GGCCTTTATCAGGACCTCCTTTTATGGCTGTATCTTCGTACCCTACGCCAGTAGCTTTTA
 P  E  I  V  L  E  E  N  T  D  I  E  A  W  D  A  V  I  E  N

AACGATAAATTATTGGAAAAGTATATCGCAGGAGAACCAATCAGCCGGGAAAAACTTGTG
                                                              1920
TTGCTATTTAATAACCTTTTCATATAGCGTCCTCTTGGTTAGTCGGCCCTTTTTGAACAC
 N  D  K  L  L  E  K  Y  I  A  G  E  P  I  S  R  E  K  L  V

CGGGAGGAACAGCGGCGGGTTCAAGACGCCTCCCTGTTCCCGGTCTATTATGGCAGCGCC
                                                              1980
GCCCTCCTTGTCGCCGCCCAAGTTCTGCGGAGGGACAAGGGCCAGATAATACCGTCGCGG
 R  E  E  Q  R  R  V  Q  D  A  S  L  F  P  V  Y  Y  G  S  A
```

TABLE 2-continued

The tetW DNA sequence flanked by the upstream transposase gene, tps, from *Bifidobacterium animalis* Bb-12 (SEQ ID NO: 22), and the complement disclosed as SEQ ID NO: 42). Transposase and Tetracycline sequences as SEQ ID NOS 40-41, respectively.

```
AAAAAGGGCCTTGGCATTCAACCGTTGATGGATGCGGTGACAGGGCTGTTCGAACCGATT
------------------------------------------------------------ 2040
TTTTTCCCGGAACCGTAAGTTGGCAACTACCTACGCCACTGTCCCGACAAGGTTGGCTAA
 K  K  G  L  G  I  Q  P  L  M  D  A  V  T  G  L  F  Q  P  I

GGGGAACAGGGGAGCGCCGCCCTATGCGGCAGCGTTTTCAAGGTGGAGTATACAGATTGC
------------------------------------------------------------ 2100
CCCCTTGTCCCCTCGCGGCGGGATACGCCGTCGCAAAAGTTCCACCTCATATGTCTAACG
 G  E  Q  G  S  A  A  L  C  G  S  V  F  K  V  E  Y  T  D  C

GGCCAGCGGCGTGTCTATCTACGGCTATACAGCGGAACGCTGCGCCTGCGGGATACGGTG
------------------------------------------------------------ 2160
CCGGTCGCCGCACAGATAGATGCCGATATGTCGCCTTGCGACGCGGACGCCCTATGCCAC
 G  Q  R  R  V  Y  L  R  L  Y  S  G  T  L  R  L  R  D  T  V

GCCCTGGCCGGGAGAGAAAAGCTGAAAATCACAGAGATGCGTATTCCATCCAAAGGGGAA
------------------------------------------------------------ 2220
CGGGACCGGCCCTCTCTTTTCGACTTTTAGTGTCTCTACGCATAAGGTAGGTTTCCCCTT
 A  L  A  G  R  E  K  L  K  I  T  S  M  R  I  P  S  K  G  E

ATTGTTCGGACAGACACCGCTTATCCGGGTGAAATTGTTATCCTTCCCAGCGACAGCGTG
------------------------------------------------------------ 2280
TAACAAGCCTGTCTGTGGCGAATAGGCCCACTTTAACAATAGGAAGGGTCGCTGTCGCAC
 I  V  R  T  D  T  A  Y  P  G  E  I  V  I  L  P  S  D  S  V

AGGTTAAACGATGTATTAGGGGACCCAACCCGGCTCCCTCGTAAAAGGTGGCGTGAGGAC
------------------------------------------------------------ 2340
TCCAATTTGCTACATAATCCCCTGGGTTGGGCCGAGGGAGCATTTTCCACCGCACTCCTG
 R  L  N  D  V  L  G  D  P  T  R  L  P  R  K  R  W  R  E  D

CCCCTCCCCATGCTGCGGACGTCGATTGCGCCGAAAACGGCAGCGCAAAGAGAACGGCTG
------------------------------------------------------------ 2400
GGGGAGGCCTACCACGCCTGCAGCTAACCCCGCTTTTCCCCTCCCCTTTCTCTTGCCCAC
 P  L  P  M  L  R  T  S  I  A  P  K  T  A  A  Q  R  E  R  L

CTGGACCCTCTTACCCAACTTCCCCATACTGACCCCCTTTTCCCCTCCCAGGTCCATTCC
------------------------------------------------------------ 2460
CACCTGCGACAATCCCTTGAACCCCTATCACTGGGCCAAAACCCCACCCTCCACCTAAGG
 L  D  A  L  T  Q  L  A  D  T  D  P  L  L  R  C  E  V  D  S

ATCACCCATGAGATCATTCTTTCTTTTTTGGGCCGGGTGCAGTTGGAGGTTGTTTCCGCT
------------------------------------------------------------ 2520
TAGTGGGTACTCTAGTAAGAAAGAAAAAACCCGGCCCACGTCAACCTCCAACAAAGGCGA
 I  T  H  E  I  I  L  S  F  L  G  R  V  Q  L  E  V  V  S  A

TTGCTGTCGGAAAAATACAAGCTTGAAACAGTGGTAAAGGAACCCACCGTCATTTATATG
------------------------------------------------------------ 2580
AACGACAGCCTTTTTATGTTCGAACTTTGTCACCATTTCCTTGGGTGGCAGTAAATATAC
 L  L  S  E  K  Y  K  L  E  T  V  V  K  E  P  T  V  T  Y  M

GAGCGGCCGCTCAAAGCAGCCAGCCACACCATCCATATCGAGGTGCCGCCCAACCCGTTT
------------------------------------------------------------ 2640
CTCGCCGGCGAGTTTCGTCGGTCGGTGTGGTAGGTATAGCTCCACGGCGGGTTGGGCAAA
 E  R  P  L  K  A  A  S  H  I  I  H  T  E  V  P  P  N  P  F

TGGGCATCCATCGGACTGTCTGTTACACCACTCCCGCTTGGCTCCGGTGTACAATACAAG
------------------------------------------------------------ 2700
ACCCGTAGGTAGCCTGACAGACAATGTGGTGAGGGCGAACCGAGGCCACATGTTATGTTC
 W  A  S  I  G  L  S  V  T  P  L  P  L  G  S  V  Q  Y  K nt 2722-T deleted in Bb12Tet-S139
AGCCGGGTTTCGCTGGGATACTTGAACCAGAGTTTTCAAAACGCTGTCAGGGATGGTATC
------------------------------------------------------------ 2760
TCGGCCCAAAGCGACCCTATGAACTTGGTCTCAAAAGTTTTGCGACAGTCCCTACCATAG
 S  R  V  S  L  C  Y  L  N  Q  S  F  Q  N  A  V  R  D  C  T
          G  Y  *  (opal)

CGTTACGGGCTGGAGCAGGGCTTGTTCGGCTGGAACGTAACGGACTGTAAGATTTGCTTT
------------------------------------------------------------ 2820
GCAATGCCCGACCTCGTCCCGAACAAGCCGACCTTGCATTGCCTGACATTCTAAACGAAA
 R  Y  G  L  E  Q  G  L  F  G  W  N  V  T  D  C  K  I  C  F

GAATACGGGCTTTATTACAGTCCGGTCAGCACGCCGGCGGACTTCCGCTCATTGGCCCCG
------------------------------------------------------------ 2880
```

TABLE 2-continued

The tetW DNA sequence flanked by the upstream transposase gene, tps, from *Bifidobacterium animalis* Bb-12 (SEQ ID NO: 22). and the complement disclosed as SEQ ID NO: 42). Transposase and Tetracycline sequences as SEQ ID NOS 40-41, respectively.

```
CTTATGCCCGAAATAATGTCAGGCCAGTCGTGCGGCCGCCTGAAGGCGAGTAACCGGGGC
 E  Y  G  L  Y  Y  S  P  V  S  T  P  A  D  F  R  S  L  A  P

ATTGTATTGGAACAGGCATTGAAGGAATCAGGGACGCAACTGCTGGAACCTTATCTCTCC
------------------------------------------------------------  2940
TAACATAACCTTGTCCGTAACTTCCTTAGTCCCTGCGTTGACGACCTTGGAATAGAGAGG
 I  V  L  E  Q  A  L  K  E  S  G  T  Q  L  L  E  P  Y  L  S

TTCACCCTCTATGCGCCCCGGGAATATCTTTCCAGGGCTTATCATGATGCACCGAAATAC
------------------------------------------------------------  3000
AAGTGGGAGATACGCGGGGCCCTTATAGAAAGGTCCCGAATAGTACTACGTGGCTTTATG
 F  T  L  Y  A  P  R  E  Y  L  S  R  A  Y  H  D  A  P  K  Y

TGTGCCACCATCGAAACGGTCCAGGTAAAAAAGGATGAAGTTGTCTTTACTGGCGAGATT
------------------------------------------------------------  3060
ACACGGTGGTAGCTTTGCCAGGTCCATTTTTTCCTACTTCAACAGAAATGACCGCTCTAA
 C  A  T  I  E  T  V  Q  V  K  K  D  E  V  V  F  T  G  E  I

CCCGCCCGCTGTATACAGGCATACCGTACTGATCTGGCCTTTTACACCAACGGGCAGAGC
------------------------------------------------------------  3120
GGGCGGGCGACATATGTCCGTATGGCATGACTAGACCGGAAAATGTGGTTGCCCGTCTCG
 P  A  R  C  I  Q  A  Y  R  T  D  L  A  F  Y  T  N  C  Q  S

GTATGCCTTACAGAACTGAAAGGGTATCAGGCCGCTGTCGGCAAGCCAGTCATCCAGCCC
------------------------------------------------------------  3180
CATACGGAATGTCTTGACTTTCCCATAGTCCGGCGACAGCCGTTCGGTCAGTAGGTCGGG
 V  C  L  T  E  L  K  G  Y  Q  A  A  V  G  K  P  V  I  Q  P

Tetracycline Stop
CGCCGTCCAAACAGCCGCCTGGACAAGGTGCGCCATATGTTCGATAAGATCACTTGATAC
------------------------------------------------------------  3240
GCGGCAGGTTTGTCGGCGGACCTGTTCCACGCGGTATACAAGTCATTCTAGTGAACTATG
 R  R  P  N  S  R  L  D  K  V  R  H  M  F  S  K  I  T  *
```

Nucleotide sequence of the inactive TetW transposon from *Bifidobacterium animalis* subsp. Lactis Bb-12 ®. The sequence was obtained by sequencing at Chr. Hansen A/S. Upstream is the transposase encoding open reading frame, nt. #4-966, with the amino acid depicted under the DNA sequence (M. W. approx. 35 kDa). The nt. sequence #1318-3234 is the tetracycline resistant encoding gene, tetW, with the amino acid outlined under the DNAsequence. (M. W. approx. 70 kDa).
The amber mutation at nt position #1741 (nt #424 relative to the start codon of tetW) for the tetracycline sensitive strain, DR10Tet-S9X (CHCC9070), is indicated above the DNA sequence.
The frameshift mutation at nt position #2722 (nt #1405 relative to the start codon) for the tetracycline sensitive strain, Bb12Tet-S139 (CHCC8902), is indicated above the DNA sequence.
*indicates a stop codon.

---

The invention claimed is:

1. A method for obtaining a tetracycline-sensitive *Bifidobacterium* strain, said method comprising:
   (a) subjecting a progenitor culture of a *Bifidobacterium* strain to a chemical mutagen and a physical mutagen; then
   (b) isolating *Bifidobacterium* cells that are sensitive to a tetracycline from said progenitor culture; and
   (c) culturing at least one tetracycline-sensitive cell of step (b) to obtain a tetracycline-sensitive *Bifidobacterium* strain,
   wherein said progenitor strain has a functional tetW gene and said tetW gene is inactivated in the obtained tetracycline-sensitive strain, and
   wherein said tetracycline-sensitive strain has a Minimum Inhibitive Concentration to tetracycline of 1.5 µg/ml or less.

2. The method according to claim 1, wherein said progenitor strain has a Minimum Inhibitive Concentration of tetracycline of at least 4 µg/ml.

3. The method according to claim 1, wherein the functional tetW gene is located on the chromosome of the progenitor *Bifidobacterium* strain.

4. The method according to claim 1, wherein the chemical mutagen is an intercalating UV-absorbing chemical and the physical mutagen is a non-ionizing radiation with a wavelength shorter than 800 nm.

5. The method according to claim 4, wherein the intercalating UV-absorbing chemical is selected from the group consisting of ethidium bromide (EtBr), ethidium, proflavine, daunomycin, adriamycin, actinomycin, ellipticine, tilorone, 4-(9-acridinylamino)-N-(methanesulfonyl-m-anisidide (m-AMSA), mithramycin, netropsin, irehdiamine A, anthramycin, steptonigrin, bleomycin, ditercalinium, triostin, and echinomycin.

6. The method according to claim 2, wherein the Minimum Inhibitive Concentration (MIC) is determined by:
   a) dipping a sterile cotton swab into a culture, which has grown overnight, of a tetracycline sensitive strain to be tested,
   b) streaking the entire surface of a MRS agar plate (diameter: 8.5 cm) evenly in three directions with the cotton swab from step a),
   c) when the inoculum applied in step b) has dried, applying to the agar surface of the agar plate, by help of a manual applicator, a plastic strip that presents a predefined, stable gradient of antibiotic concentrations, thereby defining an MIC scale, such that the MIC scale is facing upwards,
   d) inoculating the agar plate anaerobically in an inverted position at 37° C. overnight, and
   e) determining the MIC value by reading the value where the edge of the inhibition ellipse intersects the strip.

7. The method according to claim 1, wherein the progenitor *Bifidobacterium* strain is selected from the group consisting of *Bifidobacterium animalis* subspecies lactis strain CHCC5445, deposited on Sep. 30, 2003 with the Deutsche Sammlung von Mikroorganismen und Zellkulturen under accession number DSM15954, and *Bifidobacterium animalis* subspecies lactis strain CHCC7158, deposited on Apr. 28, 2005 with the Deutsche Sammlung von Mikroorganismen und Zellkulturen under accession number DSM17280.

8. The method according to claim 1, wherein step b) comprises the steps of:
   i) determining the minimum inhibitive concentration (MIC) of the bacteria by a susceptibility screening method that comprises using a plastic strip that presents a predefined, stable gradient of antibiotic conentrations, thereby defining a MIC scale,
   ii) dividing the bacteria into two classes based on the MIC result determined in i):
   Class 1: bacteria with a MIC of 1.5 µg/ml or less, and
   Class 2: bacteria with a MIC over 1.5 µg/ml; and
   iii) identifying and expanding those antibiotic sensitive bacteria identified in ii) with a MIC of 1.5 µg/ml or less (Class 1).

9. The method according to claim 8, wherein the antibiotic is tetracycline.

10. The method according to claim 1, wherein the progenitor Bifidobacteria strain is a probiotic strain.

11. The method according to claim 1, wherein the tetracycline sensitive strain obtained is a probiotic strain.

12. The method according to claim 1, wherein the method comprises the steps of:
   i) culturing the *Bifidobacterium* sp. cell comprising a functional tetW gene or that has a Minimum Inhibitive Concentration of 4 microgram of tetracycline/ml or higher to obtain a culture of exponential growing cells,
   ii) transferring an aliquot of the cells obtained in step i) to fresh medium containing ethidium bromide (EtBr),
   iii) transferring the culture obtained in step ii) to one or more containers to form a 0.5-10 mm thick layer of culture,
   iv) subjecting the culture(s) of step iii) to a UV treatment,
   v) culturing the mutated cells obtained from step iv) to obtain a culture of exponential growing cells,
   vi) transferring an aliquot of bacteria to one or more petridishes containing a suitable agar growth medium, the aliquot of bacteria are selected to give single colonies,
   vii) identifying those colonies from step vi) that have acquired antibiotic sensitivity by replica plating to petridishes with and without antibiotic, and
   viii) isolating and expanding the cell obtained in step vii).

13. The method according to claim 12, wherein the culture obtained in step iv) is subjected to an enrichment step for mutations comprising the steps of:
   iva) transferring an aliquot of the UV treated culture to fresh medium containing a dose of a penicillin analogue which is detrimental to exponentially growing cells, but tolerable to non-growing cells, and
   ivb) culturing the cells in said penicillin analogue comprising medium under conditions, which would promote exponential growth in the absence of penicillin or an analogue of penicillin.

14. The method according to claim 13, wherein the UV-treatment of step iv) reduces the number of living cells measured by Colony Forming Units (CFUs) to less than 20% relative to the number of the CFUs of the culture immediately before the UV-treatment.

15. The method according to claim 13, wherein the penicillin analogue is ampicillin being used at a dose of 50-300 ug/ml medium.

16. The method according to claim 1, wherein the tetracycline is selected from the group of tetracycline, demeclocycline, meclocycline, doxycycline, lymecycline, methacycline, minocycline, oxytetracycline, rolitetracycline, and chlortetracycline.

17. The method according to claim 1, wherein the progenitor *Bifidobacterium* strain is selected from the group consisting of *Bifidobacteriacea* comprising *Bifidobacterium longum*, *Bifidobacterium pseudocatenulatum*, *Bifidobacterium bifidum*, *Bifidobacterium lactis*, *Bifidobacterium animalis* and subspecies thereof.

18. The method according to claim 1, wherein the progenitor *Bifidobacterium* strain is *Bifidobacterium animalis* subspecies *lactis*.

19. The method according to claim 1, wherein the Minimum inhibitive Concentration (MIC) of tetracycline of the progenitor *Bifidobacterium* strain is at least 10-fold higher than the MIC of the tetracycline sensitive strain obtained.

20. The method according to claim 1, wherein the Minimum inhibitive Concentration (MIC) of tetracycline of the progenitor *Bifidobacterium* strain is at least 10 microgram/ml and the MIC of tetracycline of the tetracycline sensitive strain obtained is 1 microgram/ml or less.

* * * * *

SEQUENCE LISTING

<160> NUMBER OF SEQ ID NOS: 42

<210> SEQ ID NO 1
<211> LENGTH: 24
<212> TYPE: DNA
<213> ORGANISM: Bifidobacterium animalis
<220> FEATURE:
<221> NAME/KEY: CDS
<222> LOCATION: (1)..(24)

<400> SEQUENCE: 1 tcg ctg gga tac ttg aac cag agt                              24
Ser Leu Gly Tyr Leu Asn Gln Ser
 1               5

<210> SEQ ID NO 2
<211> LENGTH: 24
<212> TYPE: DNA
<213> ORGANISM: Bifidobacterium animalis
<220> FEATURE:

```
<221> NAME/KEY: CDS
<222> LOCATION: (1)..(12)

<400> SEQUENCE: 2 tcg ctg gga tac tgaaccagag tt                                         24
Ser Leu Gly Tyr
  1

<210> SEQ ID NO 3
<211> LENGTH: 12
<212> TYPE: DNA
<213> ORGANISM: Bifidobacterium animalis

<400> SEQUENCE: 3
ggatactgaa cc                                                         12

<210> SEQ ID NO 4
<211> LENGTH: 24
<212> TYPE: DNA
<213> ORGANISM: Bifidobacterium animalis
<220> FEATURE:
<221> NAME/KEY: CDS
<222> LOCATION: (1)..(24)

<400> SEQUENCE: 4 cag agc gtg gtt cag tct gtt cgg                                       24
Gln Ser Val Val Gln Ser Val Arg
  1               5

<210> SEQ ID NO 5
<211> LENGTH: 24
<212> TYPE: DNA
<213> ORGANISM: Bifidobacterium animalis
<220> FEATURE:
<221> NAME/KEY: CDS
<222> LOCATION: (1)..(12)

<400> SEQUENCE: 5 cag agc gtg gtt tagtctgttc gg                                         24
Gln Ser Val Val
  1

<210> SEQ ID NO 6
<211> LENGTH: 12
<212> TYPE: DNA
<213> ORGANISM: Bifidobacterium animalis

<400> SEQUENCE: 6
gtggtttagt ct                                                         12

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gagcatcgct taattccttc gagggg                                          26

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
cgaggggact ttggcccacc gctgggtgg                                           29

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcaggcaggc acgtccatcc gcctc                                               25

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggcttctgcc accgtggcct cgtcac                                              26

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cctgtccttg tccacgccga tatgcgc                                             27

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cggcacctgc tgtataatgc ggattgtggc                                          30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtgggaacaa aggattatga tagtccc                                             27

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
```
ggctggcgtt gatttgcaga gcgtgg                                    26

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcagacggtg tcgctgtccc cgg                                       23

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccggggacag cgacaccgtc tgc                                       23

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggagcggccg ctcaaagcag ccagcc                                    26

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggctggctgc tttgagcggc cgctcc                                    26

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcccaaaacg ggttgggcgg cacctcg                                   27

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccagcccgta acggatacca tccc                                      24

-continued

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gatggtcgca tgatcggcgg ggtcactccc                                    30

<210> SEQ ID NO 22
<211> LENGTH: 3240
<212> TYPE: DNA
<213> ORGANISM: Bifidobacterium animalis
<220> FEATURE:
<221> NAME/KEY: CDS
<222> LOCATION: (4)..(966)
<220> FEATURE:
<221> NAME/KEY: CDS
<222> LOCATION: (1318)..(3234)

<400> SEQUENCE: 22

```
cag atg acg att tcc gca ttc agc gac gaa ctg gca cag gtg cgg acg      48
    Met Thr Ile Ser Ala Phe Ser Asp Glu Leu Ala Gln Val Arg Thr
    1               5                   10                  15 aag aaa aaa gca ttt ctc gac cag att gaa cgg atc gtc ccg tgg aag      96
Lys Lys Lys Ala Phe Leu Asp Gln Ile Glu Arg Ile Val Pro Trp Lys
            20                  25                  30 gaa tgg ctt gcc atg att cag ccg tgc tat tac aaa gga gag cgc ggc     144
Glu Trp Leu Ala Met Ile Gln Pro Cys Tyr Tyr Lys Gly Glu Arg Gly
        35                  40                  45 aac aaa ccc tat ccg ctg gag atc atg ctc cga ctg tat ctg ctg caa     192
Asn Lys Pro Tyr Pro Leu Glu Ile Met Leu Arg Leu Tyr Leu Leu Gln
    50                  55                  60 aac ctc tat gac ctg agt gac gag gcc acg gtg gca gaa gcc atc gac     240
Asn Leu Tyr Asp Leu Ser Asp Glu Ala Thr Val Ala Glu Ala Ile Asp
65                  70                  75 agc cgc gca ttt tcg gag ttc tgc ggc gtc gat tcc agc aac cag gtt     288
Ser Arg Ala Phe Ser Glu Phe Cys Gly Val Asp Ser Ser Asn Gln Val
    80                  85                  90                  95 ccg aac ggg gat act ctt ggc cgg ttc cgg aac ttg ctg atc aag aac     336
Pro Asn Gly Asp Thr Leu Gly Arg Phe Arg Asn Leu Leu Ile Lys Asn
                100                 105                 110 gga ctg cag gag aag ctg ttc gct cag gtg gta gca gcg ctc atg gaa     384
Gly Leu Gln Glu Lys Leu Phe Ala Gln Val Val Ala Ala Leu Met Glu
            115                 120                 125 cgt ggc ctc att ctg aaa aag ggc acc att gta gat tcc acc atc att     432
Arg Gly Leu Ile Leu Lys Lys Gly Thr Ile Val Asp Ser Thr Ile Ile
        130                 135                 140 tcc gcc ccc tct tct acc aag aat aag gaa aag aaa cgg gat ccg gat     480
Ser Ala Pro Ser Ser Thr Lys Asn Lys Glu Lys Lys Arg Asp Pro Asp
    145                 150                 155 gcc cac caa gtc aag aag ggc aac acc tgg cac ttt ggg tac aaa gcg     528
Ala His Gln Val Lys Lys Gly Asn Thr Trp His Phe Gly Tyr Lys Ala
160                 165                 170                 175 cat atc ggc gtg gac aag gac agc gga ctg gtt cac aca gtg gaa gct     576
His Ile Gly Val Asp Lys Asp Ser Gly Leu Val His Thr Val Glu Ala
                180                 185                 190 aca ccg gca aat gtc cac gac gtt gcg gaa gtg ccg aaa tta ttg acg     624
Thr Pro Ala Asn Val His Asp Val Ala Glu Val Pro Lys Leu Leu Thr
            195                 200                 205
```

-continued

| | |
|---|---|
| gga gag gaa gaa aca gtc tat gga gac agc ggt tat ctc ggc gca ggt<br>Gly Glu Glu Glu Thr Val Tyr Gly Asp Ser Gly Tyr Leu Gly Ala Gly<br>210               215               220 | 672 |
| aag cgc gaa gat gcc gta gtc cga aac aaa gct ggc cgg aaa atc aag<br>Lys Arg Glu Asp Ala Val Val Arg Asn Lys Ala Gly Arg Lys Ile Lys<br>225               230               235 | 720 |
| tac aag atc aat cgt cgt cca tcg cag atg aag aaa ctg agc aaa agc<br>Tyr Lys Ile Asn Arg Arg Pro Ser Gln Met Lys Lys Leu Ser Lys Ser<br>240               245            250             255 | 768 |
| ggg cag tac gca gca aag aaa gcg gaa cgg gcg aaa tcc tca gtg cga<br>Gly Gln Tyr Ala Ala Lys Lys Ala Glu Arg Ala Lys Ser Ser Val Arg<br>260             265             270 | 816 |
| gca aaa gta gag cat gta ttc ggt gtc gtt aag aag cag ctg cgc ttc<br>Ala Lys Val Glu His Val Phe Gly Val Val Lys Lys Gln Leu Arg Phe<br>275             280             285 | 864 |
| cga aaa acg cga tac cga ggg ctt gaa aag caa caa gcc aaa ttc aat<br>Arg Lys Thr Arg Tyr Arg Gly Leu Glu Lys Gln Gln Ala Lys Phe Asn<br>290             295            300 | 912 |
| atc atg ttt gcg ttg gca aat ctg att ctg gct gac aga ccc tgt ctg<br>Ile Met Phe Ala Leu Ala Asn Leu Ile Leu Ala Asp Arg Pro Cys Leu<br>305             310             315 | 960 |
| gca gct tgagtcagtg cgcctttgcg gacaaaaaat tcggaggtta tccacagttt<br>Ala Ala<br>320 | 1016 |
| ttattcggca cctgctgtat aatgcggatt gtggcatttg tgcggtgttg ccttaaataa | 1076 |
| aactataatc aaatagtggg aacaaaggat tatgatagtc cctttgtag gggcttagtt | 1136 |
| ttttgtaccc aatttaagaa tacttttgcc ttatcaattt tgacatatcc ccaaaaacag | 1196 |
| cactcacaaa caggtgtatg ctgtatatgt gtatgtccgc aaattatcat ccccagtggt | 1256 |
| aaaagtattt tactgctggg gatttttatg cccttcgggg cagtaaaggg aggacaatca | 1316 |
| c atg aaa ata atc aat att gga att ctt gcc cat gta gac gct gga aag<br>  Met Lys Ile Ile Asn Ile Gly Ile Leu Ala His Val Asp Ala Gly Lys<br>             325             330             335 | 1365 |
| acg acc ttg acg gag agc ctg cta tat gcc agc gga gcc att tca gaa<br>Thr Thr Leu Thr Glu Ser Leu Leu Tyr Ala Ser Gly Ala Ile Ser Glu<br>340             345             350 | 1413 |
| ccg ggg agc gtc gaa aaa ggg aca acg agg acg gac acc atg ctt ttg<br>Pro Gly Ser Val Glu Lys Gly Thr Thr Arg Thr Asp Thr Met Leu Leu<br>355             360             365 | 1461 |
| gag cgg cag cgt ggg att acc att caa gcg gca gtc act tcc ttc cag<br>Glu Arg Gln Arg Gly Ile Thr Ile Gln Ala Ala Val Thr Ser Phe Gln<br>370               375            380             385 | 1509 |
| tgg cac aga tgt aaa gtc aac att gtg gat acg ccc ggc cac atg gat<br>Trp His Arg Cys Lys Val Asn Ile Val Asp Thr Pro Gly His Met Asp<br>390             395             400 | 1557 |
| ttt ttg gcg gag gtg tac cgc tct ttg gct gtt tta gat ggg gcc atc<br>Phe Leu Ala Glu Val Tyr Arg Ser Leu Ala Val Leu Asp Gly Ala Ile<br>405             410             415 | 1605 |
| ttg gtg atc tcc gct aaa gat ggc gtg cag gcc cag acc cgt att ctg<br>Leu Val Ile Ser Ala Lys Asp Gly Val Gln Ala Gln Thr Arg Ile Leu<br>420             425             430 | 1653 |
| ttc cat gcc ctg cgg aaa atg aac att ccc acc gtt atc ttt atc aac<br>Phe His Ala Leu Arg Lys Met Asn Ile Pro Thr Val Ile Phe Ile Asn<br>435             440             445 | 1701 |
| aag atc gac cag gct ggc gtt gat ttg cag agc gtg gtt cag tct gtt<br>Lys Ile Asp Gln Ala Gly Val Asp Leu Gln Ser Val Val Gln Ser Val<br>450             455             460             465 | 1749 |
| cgg gat aag ctc tcc gcc gat att atc atc aag cag acg gtg tcg ctg<br>Arg Asp Lys Leu Ser Ala Asp Ile Ile Ile Lys Gln Thr Val Ser Leu | 1797 |

```
                      470                 475                 480
tcc ccg gaa ata gtc ctg gag gaa aat acc gac ata gaa gca tgg gat    1845
Ser Pro Glu Ile Val Leu Glu Glu Asn Thr Asp Ile Glu Ala Trp Asp
            485                 490                 495 gcg gtc atc gaa aat aac gat aaa tta ttg gaa aag tat atc gca gga    1893
Ala Val Ile Glu Asn Asn Asp Lys Leu Leu Glu Lys Tyr Ile Ala Gly
        500                 505                 510 gaa cca atc agc cgg gaa aaa ctt gtg cgg gag gaa cag cgg cgg gtt    1941
Glu Pro Ile Ser Arg Glu Lys Leu Val Arg Glu Glu Gln Arg Arg Val
    515                 520                 525 caa gac gcc tcc ctg ttc ccg gtc tat tat ggc agc gcc aaa aag ggc    1989
Gln Asp Ala Ser Leu Phe Pro Val Tyr Tyr Gly Ser Ala Lys Lys Gly
530                 535                 540                 545 ctt ggc att caa ccg ttg atg gat gcg gtc aca ggg ctg ttc caa ccg    2037
Leu Gly Ile Gln Pro Leu Met Asp Ala Val Thr Gly Leu Phe Gln Pro
                550                 555                 560 att ggg gaa cag ggg agc gcc gcc cta tgc ggc agc gtt ttc aag gtg    2085
Ile Gly Glu Gln Gly Ser Ala Ala Leu Cys Gly Ser Val Phe Lys Val
            565                 570                 575 gag tat aca gat tgc ggc cag cgg cgt gtc tat cta cgg cta tac agc    2133
Glu Tyr Thr Asp Cys Gly Gln Arg Arg Val Tyr Leu Arg Leu Tyr Ser
        580                 585                 590 gga acg ctg cgc ctg cgg gat acg gtg gcc ctg gcc ggg aga gaa aag    2181
Gly Thr Leu Arg Leu Arg Asp Thr Val Ala Leu Ala Gly Arg Glu Lys
    595                 600                 605 ctg aaa atc aca gag atg cgt att cca tcc aaa ggg gaa att gtt cgg    2229
Leu Lys Ile Thr Glu Met Arg Ile Pro Ser Lys Gly Glu Ile Val Arg
610                 615                 620                 625 aca gac acc gct tat ccg ggt gaa att gtt atc ctt ccc agc gac agc    2277
Thr Asp Thr Ala Tyr Pro Gly Glu Ile Val Ile Leu Pro Ser Asp Ser
                630                 635                 640 gtg agg tta aac gat gta tta ggg gac cca acc cgg ctc cct cgt aaa    2325
Val Arg Leu Asn Asp Val Leu Gly Asp Pro Thr Arg Leu Pro Arg Lys
            645                 650                 655 agg tgg cgt gag gac ccc ctc ccc atg ctg cgg acg tcg att gcg ccg    2373
Arg Trp Arg Glu Asp Pro Leu Pro Met Leu Arg Thr Ser Ile Ala Pro
        660                 665                 670 aaa acg gca gcg caa aga gaa cgg ctg ctg gac gct ctt acg caa ctt    2421
Lys Thr Ala Ala Gln Arg Glu Arg Leu Leu Asp Ala Leu Thr Gln Leu
    675                 680                 685 gcg gat act gac ccg ctt ttg cgc tgc gag gtg gat tcc atc acc cat    2469
Ala Asp Thr Asp Pro Leu Leu Arg Cys Glu Val Asp Ser Ile Thr His
690                 695                 700                 705 gag atc att ctt tct ttt ttg ggc cgg gtg cag ttg gag gtt gtt tcc    2517
Glu Ile Ile Leu Ser Phe Leu Gly Arg Val Gln Leu Glu Val Val Ser
                710                 715                 720 gct ttg ctg tcg gaa aaa tac aag ctt gaa aca gtg gta aag gaa ccc    2565
Ala Leu Leu Ser Glu Lys Tyr Lys Leu Glu Thr Val Val Lys Glu Pro
            725                 730                 735 acc gtc att tat atg gag cgg ccg ctc aaa gca gcc agc cac acc atc    2613
Thr Val Ile Tyr Met Glu Arg Pro Leu Lys Ala Ala Ser His Thr Ile
        740                 745                 750 cat atc gag gtg ccg ccc aac ccg ttt tgg gca tcc atc gga ctg tct    2661
His Ile Glu Val Pro Pro Asn Pro Phe Trp Ala Ser Ile Gly Leu Ser
    755                 760                 765 gtt aca cca ctc ccg ctt ggc tcc ggt gta caa tac aag agc cgg gtt    2709
Val Thr Pro Leu Pro Leu Gly Ser Gly Val Gln Tyr Lys Ser Arg Val
770                 775                 780                 785 tcg ctg gga tac ttg aac cag agt ttt caa aac gct gtc agg gat ggt    2757
Ser Leu Gly Tyr Leu Asn Gln Ser Phe Gln Asn Ala Val Arg Asp Gly
```

```
                                 790                 795                 800
atc cgt tac ggg ctg gag cag ggc ttg ttc ggc tgg aac gta acg gac         2805
Ile Arg Tyr Gly Leu Glu Gln Gly Leu Phe Gly Trp Asn Val Thr Asp
            805                 810                 815 tgt aag att tgc ttt gaa tac ggg ctt tat tac agt ccg gtc agc acg         2853
Cys Lys Ile Cys Phe Glu Tyr Gly Leu Tyr Tyr Ser Pro Val Ser Thr
            820                 825                 830 ccg gcg gac ttc cgc tca ttg gcc ccg att gta ttg gaa cag gca ttg         2901
Pro Ala Asp Phe Arg Ser Leu Ala Pro Ile Val Leu Glu Gln Ala Leu
            835                 840                 845 aag gaa tca ggg acg caa ctg ctg gaa cct tat ctc tcc ttc acc ctc         2949
Lys Glu Ser Gly Thr Gln Leu Leu Glu Pro Tyr Leu Ser Phe Thr Leu
850                 855                 860                 865 tat gcg ccc cgg gaa tat ctt tcc agg gct tat cat gat gca ccg aaa         2997
Tyr Ala Pro Arg Glu Tyr Leu Ser Arg Ala Tyr His Asp Ala Pro Lys
                870                 875                 880 tac tgt gcc acc atc gaa acg gtc cag gta aaa aag gat gaa gtt gtc         3045
Tyr Cys Ala Thr Ile Glu Thr Val Gln Val Lys Lys Asp Glu Val Val
            885                 890                 895 ttt act ggc gag att ccc gcc cgc tgt ata cag gca tac cgt act gat         3093
Phe Thr Gly Glu Ile Pro Ala Arg Cys Ile Gln Ala Tyr Arg Thr Asp
            900                 905                 910 ctg gcc ttt tac acc aac ggg cag agc gta tgc ctt aca gaa ctg aaa         3141
Leu Ala Phe Tyr Thr Asn Gly Gln Ser Val Cys Leu Thr Glu Leu Lys
            915                 920                 925 ggg tat cag gcc gct gtc ggc aag cca gtc atc cag ccc cgc cgt cca         3189
Gly Tyr Gln Ala Ala Val Gly Lys Pro Val Ile Gln Pro Arg Arg Pro
930                 935                 940                 945 aac agc cgc ctg gac aag gtg cgc cat atg ttc agt aag atc act             3234
Asn Ser Arg Leu Asp Lys Val Arg His Met Phe Ser Lys Ile Thr
                950                 955                 960 tgatac                                                                  3240

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caatacaaga gccgggtttc                                                   20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgctgaccg gactgtaata aa                                                22

<210> SEQ ID NO 25
<211> LENGTH: 11
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
```

```
atactgaacc a                                                    11

<210> SEQ ID NO 26
<211> LENGTH: 24
<212> TYPE: DNA
<213> ORGANISM: Bifidobacterium animalis
<220> FEATURE:
<221> NAME/KEY: CDS
<222> LOCATION: (1)..(24)

<400> SEQUENCE: 26 tac ttg aac cag cgt ttt caa aac                                 24
Tyr Leu Asn Gln Arg Phe Gln Asn
  1               5

<210> SEQ ID NO 27
<211> LENGTH: 12
<212> TYPE: DNA
<213> ORGANISM: Bifidobacterium animalis

<400> SEQUENCE: 27
accagcgttt tc                                                   12

<210> SEQ ID NO 28
<211> LENGTH: 12
<212> TYPE: DNA
<213> ORGANISM: Bifidobacterium animalis

<400> SEQUENCE: 28
cgccctgcca ca                                                   12

<210> SEQ ID NO 29
<211> LENGTH: 12
<212> TYPE: DNA
<213> ORGANISM: Bifidobacterium animalis

<400> SEQUENCE: 29
atattgtcat ca                                                   12

<210> SEQ ID NO 30
<211> LENGTH: 12
<212> TYPE: DNA
<213> ORGANISM: Bifidobacterium animalis

<400> SEQUENCE: 30
tagacgatgg aa                                                   12

<210> SEQ ID NO 31
<211> LENGTH: 12
<212> TYPE: DNA
<213> ORGANISM: Bifidobacterium animalis

<400> SEQUENCE: 31
cggtccgggt aa                                                   12

<210> SEQ ID NO 32
<211> LENGTH: 13
<212> TYPE: DNA
<213> ORGANISM: Bifidobacterium animalis

<400> SEQUENCE: 32
ctgatccggc ctt                                                  13

<210> SEQ ID NO 33
```

```
<211> LENGTH: 8
<212> TYPE: PRT
<213> ORGANISM: Bifidobacterium animalis

<400> SEQUENCE: 33

Ser Leu Gly Tyr Leu Asn Gln Ser
1               5

<210> SEQ ID NO 34
<211> LENGTH: 4
<212> TYPE: PRT
<213> ORGANISM: Bifidobacterium animalis

<400> SEQUENCE: 34

Ser Leu Gly Tyr
1

<210> SEQ ID NO 35
<211> LENGTH: 8
<212> TYPE: PRT
<213> ORGANISM: Bifidobacterium animalis

<400> SEQUENCE: 35

Gln Ser Val Val Gln Ser Val Arg
1               5

<210> SEQ ID NO 36
<211> LENGTH: 4
<212> TYPE: PRT
<213> ORGANISM: Bifidobacterium animalis

<400> SEQUENCE: 36

Gln Ser Val Val
1

<210> SEQ ID NO 37
<211> LENGTH: 24
<212> TYPE: DNA
<213> ORGANISM: Bifidobacterium animalis
<220> FEATURE:
<221> NAME/KEY: CDS
<222> LOCATION: (1)..(24)

<400> SEQUENCE: 37 tac ttg aac cag agt ttt caa aac                          24
Tyr Leu Asn Gln Ser Phe Gln Asn
  1               5

<210> SEQ ID NO 38
<211> LENGTH: 8
<212> TYPE: PRT
<213> ORGANISM: Bifidobacterium animalis

<400> SEQUENCE: 38

Tyr Leu Asn Gln Ser Phe Gln Asn
1               5

<210> SEQ ID NO 39
<211> LENGTH: 8
<212> TYPE: PRT
<213> ORGANISM: Bifidobacterium animalis

<400> SEQUENCE: 39

Tyr Leu Asn Gln Arg Phe Gln Asn
1               5
```

```
<210> SEQ ID NO 40
<211> LENGTH: 321
<212> TYPE: PRT
<213> ORGANISM: Bifidobacterium animalis

<400> SEQUENCE: 40

Met Thr Ile Ser Ala Phe Ser Asp Glu Leu Ala Gln Val Arg Thr Lys
1               5                   10                  15

Lys Lys Ala Phe Leu Asp Gln Ile Glu Arg Ile Val Pro Trp Lys Glu
            20                  25                  30

Trp Leu Ala Met Ile Gln Pro Cys Tyr Tyr Lys Gly Glu Arg Gly Asn
        35                  40                  45

Lys Pro Tyr Pro Leu Glu Ile Met Leu Arg Leu Tyr Leu Leu Gln Asn
    50                  55                  60

Leu Tyr Asp Leu Ser Asp Glu Ala Thr Val Ala Glu Ala Ile Asp Ser
65                  70                  75                  80

Arg Ala Phe Ser Glu Phe Cys Gly Val Asp Ser Ser Asn Gln Val Pro
                85                  90                  95

Asn Gly Asp Thr Leu Gly Arg Phe Arg Asn Leu Leu Ile Lys Asn Gly
            100                 105                 110

Leu Gln Glu Lys Leu Phe Ala Gln Val Val Ala Ala Leu Met Glu Arg
        115                 120                 125

Gly Leu Ile Leu Lys Lys Gly Thr Ile Val Asp Ser Thr Ile Ile Ser
130                 135                 140

Ala Pro Ser Ser Thr Lys Asn Lys Glu Lys Lys Arg Asp Pro Asp Ala
145                 150                 155                 160

His Gln Val Lys Lys Gly Asn Thr Trp His Phe Gly Tyr Lys Ala His
                165                 170                 175

Ile Gly Val Asp Lys Asp Ser Gly Leu Val His Thr Val Glu Ala Thr
            180                 185                 190

Pro Ala Asn Val His Asp Val Ala Glu Val Pro Lys Leu Leu Thr Gly
        195                 200                 205

Glu Glu Thr Val Tyr Gly Asp Ser Gly Tyr Leu Gly Ala Gly Lys
    210                 215                 220

Arg Glu Asp Ala Val Val Arg Asn Lys Ala Gly Arg Lys Ile Lys Tyr
225                 230                 235                 240

Lys Ile Asn Arg Arg Pro Ser Gln Met Lys Lys Leu Ser Lys Ser Gly
                245                 250                 255

Gln Tyr Ala Ala Lys Lys Ala Glu Arg Ala Lys Ser Ser Val Arg Ala
            260                 265                 270

Lys Val Glu His Val Phe Gly Val Val Lys Lys Gln Leu Arg Phe Arg
        275                 280                 285

Lys Thr Arg Tyr Arg Gly Leu Glu Lys Gln Gln Ala Lys Phe Asn Ile
    290                 295                 300

Met Phe Ala Leu Ala Asn Leu Ile Leu Ala Asp Arg Pro Cys Leu Ala
305                 310                 315                 320

Ala

<210> SEQ ID NO 41
<211> LENGTH: 639
<212> TYPE: PRT
<213> ORGANISM: Bifidobacterium animalis

<400> SEQUENCE: 41

Met Lys Ile Ile Asn Ile Gly Ile Leu Ala His Val Asp Ala Gly Lys
1               5                   10                  15
```

```
Thr Thr Leu Thr Glu Ser Leu Leu Tyr Ala Ser Gly Ala Ile Ser Glu
         20                  25                  30

Pro Gly Ser Val Glu Lys Gly Thr Arg Thr Asp Thr Met Leu Leu
             35                  40                  45

Glu Arg Gln Arg Gly Ile Thr Ile Gln Ala Ala Val Thr Ser Phe Gln
 50                  55                  60

Trp His Arg Cys Lys Val Asn Ile Val Asp Thr Pro Gly His Met Asp
 65                  70                  75                  80

Phe Leu Ala Glu Val Tyr Arg Ser Leu Ala Val Leu Asp Gly Ala Ile
                 85                  90                  95

Leu Val Ile Ser Ala Lys Asp Gly Val Gln Ala Gln Thr Arg Ile Leu
                100                 105                 110

Phe His Ala Leu Arg Lys Met Asn Ile Pro Thr Val Ile Phe Ile Asn
                115                 120                 125

Lys Ile Asp Gln Ala Gly Val Asp Leu Gln Ser Val Val Gln Ser Val
        130                 135                 140

Arg Asp Lys Leu Ser Ala Asp Ile Ile Ile Lys Gln Thr Val Ser Leu
145                 150                 155                 160

Ser Pro Glu Ile Val Leu Glu Glu Asn Thr Asp Ile Glu Ala Trp Asp
                165                 170                 175

Ala Val Ile Glu Asn Asn Asp Lys Leu Leu Glu Lys Tyr Ile Ala Gly
                180                 185                 190

Glu Pro Ile Ser Arg Glu Lys Leu Val Arg Glu Gln Arg Arg Val
                195                 200                 205

Gln Asp Ala Ser Leu Phe Pro Val Tyr Tyr Gly Ser Ala Lys Lys Gly
        210                 215                 220

Leu Gly Ile Gln Pro Leu Met Asp Ala Val Thr Gly Leu Phe Gln Pro
225                 230                 235                 240

Ile Gly Glu Gln Gly Ser Ala Ala Leu Cys Gly Ser Val Phe Lys Val
                245                 250                 255

Glu Tyr Thr Asp Cys Gly Gln Arg Arg Val Tyr Leu Arg Leu Tyr Ser
                260                 265                 270

Gly Thr Leu Arg Leu Arg Asp Thr Val Ala Leu Ala Gly Arg Glu Lys
        275                 280                 285

Leu Lys Ile Thr Glu Met Arg Ile Pro Ser Lys Gly Glu Ile Val Arg
290                 295                 300

Thr Asp Thr Ala Tyr Pro Gly Glu Ile Val Ile Leu Pro Ser Asp Ser
305                 310                 315                 320

Val Arg Leu Asn Asp Val Leu Gly Asp Pro Thr Arg Leu Pro Arg Lys
                325                 330                 335

Arg Trp Arg Glu Asp Pro Leu Pro Met Leu Arg Thr Ser Ile Ala Pro
                340                 345                 350

Lys Thr Ala Ala Gln Arg Glu Arg Leu Leu Asp Ala Leu Thr Gln Leu
        355                 360                 365

Ala Asp Thr Asp Pro Leu Leu Arg Cys Glu Val Asp Ser Ile Thr His
370                 375                 380

Glu Ile Ile Leu Ser Phe Leu Gly Arg Val Gln Leu Glu Val Val Ser
385                 390                 395                 400

Ala Leu Leu Ser Glu Lys Tyr Lys Leu Glu Thr Val Val Lys Glu Pro
                405                 410                 415

Thr Val Ile Tyr Met Glu Arg Pro Leu Lys Ala Ala Ser His Thr Ile
                420                 425                 430

His Ile Glu Val Pro Pro Asn Pro Phe Trp Ala Ser Ile Gly Leu Ser
        435                 440                 445
```

| | | | | | | | | | | | | |
|---|---|---|---|---|---|---|---|---|---|---|---|---|
|Val|Thr|Pro|Leu|Pro|Leu|Gly|Ser|Gly|Val|Gln|Tyr|Lys|Ser|Arg|Val|
| |450| | | | |455| | | | |460| | | | |

Ser Leu Gly Tyr Leu Asn Gln Ser Phe Gln Asn Ala Val Arg Asp Gly
465                 470                 475                 480

Ile Arg Tyr Gly Leu Glu Gln Gly Leu Phe Gly Trp Asn Val Thr Asp
                485                 490                 495

Cys Lys Ile Cys Phe Glu Tyr Gly Leu Tyr Tyr Ser Pro Val Ser Thr
            500                 505                 510

Pro Ala Asp Phe Arg Ser Leu Ala Pro Ile Val Leu Glu Gln Ala Leu
        515                 520                 525

Lys Glu Ser Gly Thr Gln Leu Leu Glu Pro Tyr Leu Ser Phe Thr Leu
530                 535                 540

Tyr Ala Pro Arg Glu Tyr Leu Ser Arg Ala Tyr His Asp Ala Pro Lys
545                 550                 555                 560

Tyr Cys Ala Thr Ile Glu Thr Val Gln Val Lys Lys Asp Glu Val Val
                565                 570                 575

Phe Thr Gly Glu Ile Pro Ala Arg Cys Ile Gln Ala Tyr Arg Thr Asp
            580                 585                 590

Leu Ala Phe Tyr Thr Asn Gly Gln Ser Val Cys Leu Thr Glu Leu Lys
        595                 600                 605

Gly Tyr Gln Ala Ala Val Gly Lys Pro Val Ile Gln Pro Arg Arg Pro
610                 615                 620

Asn Ser Arg Leu Asp Lys Val Arg His Met Phe Ser Lys Ile Thr
625                 630                 635

<210> SEQ ID NO 42
<211> LENGTH: 3240
<212> TYPE: DNA
<213> ORGANISM: Bifidobacterium animalis

<400> SEQUENCE: 42

```
gtatcaagtg atcttactga acatatggcg caccttgtcc aggcggctgt ttggacggcg    60
gggctggatg actggcttgc cgacagcggc ctgataccct ttcagttctg taaggcatac   120
gctctgcccg ttggtgtaaa aggccagatc agtacggtat gcctgtatac agcgggcggg   180
aatctcgcca gtaaagacaa cttcatcctt ttttacctgg accgtttcga tggtggcaca   240
gtatttcggt gcatcatgat aagccctgga agatattccc ggggcgcat agagggtgaa    300
ggagagataa ggttccagca gttgcgtccc tgattccttc aatgcctgtt ccaatacaat   360
cggggccaat gagcggaagt ccgccggcgt gctgaccgga ctgtaataaa gcccgtattc   420
aaagcaaatc ttacagtccg ttacgttcca gccgaacaag ccctgctcca gcccgtaacg   480
gataccatcc ctgacagcgt tttgaaaact ctggttcaag tatcccagcg aaacccggct   540
cttgtattgt acaccggagc caagcgggag tggtgtaaca gacagtccga tggatgccca   600
aaacggggttg gcggcacct cgatatggat ggtgtggctg ctgctttga gcggccgctc   660
catataaatg acggtgggtt cctttaccac tgtttcaagc ttgtattttt ccgacagcaa   720
agcggaaaca acctccaact gcacccggcc caaaaagaa agaatgatct catgggtgat    780
ggaatccacc tcgcagcgca aaagcgggtc agtatccgca agttgcgtaa gagcgtccag   840
cagccgttct ctttgcgctg ccgttttcgg cgcaatcgac gtccgcagca tggggagggg   900
gtcctcacgc cacctttttac gagggagccg ggttgggtcc cctaatacat cgtttaacct   960
cacgctgtcg ctgggaagga taacaatttc acccggataa gcgtgtgtct tccgaacaat  1020
ttccccttttg gatggaatac gcatctctgt gattttcagc ttttctctcc cggccagggc  1080
```

| | |
|---|---|
| caccgtatcc cgcaggcgca gcgttccgct gtatagccgt agatagacac gccgctggcc | 1140 |
| gcaatctgta tactccacct tgaaaacgct gccgcatagg gcggcgctcc cctgttcccc | 1200 |
| aatcggttgg aacagccctg tcaccgcatc catcaacggt tgaatgccaa ggcccttttt | 1260 |
| ggcgctgcca taatagaccg ggaacaggga ggcgtcttga acccgccgct gttcctcccg | 1320 |
| cacaagtttt tcccggctga ttggttctcc tgcgatatac ttttccaata atttatcgtt | 1380 |
| attttcgatg accgcatccc atgcttctat gtcggtattt tcctccagga ctatttccgg | 1440 |
| ggacagcgac accgtctgct tgatgataat atcggcggag agcttatccc gaacagactg | 1500 |
| aaccacgctc tgcaaatcaa cgccagcctg gtcgatcttg ttgataaaga taacggtggg | 1560 |
| aatgttcatt tccgcaggg catggaacag aatacgggtc tgggcctgca cgccatcttt | 1620 |
| agcggagatc accaagatgg ccccatctaa acagccaaa gagcggtaca cctccgccaa | 1680 |
| aaaatccatg tggccgggcg tatccacaat gttgacttta catctgtgcc actggaagga | 1740 |
| agtgactgcc gcttgaatgg taatcccacg ctgccgctcc aaaagcatgg tgtccgtcct | 1800 |
| cgttgtccct ttttcgacgc tccccggttc tgaaatggct ccgctggcat atagcaggct | 1860 |
| ctccgtcaag gtcgtctttc cagcgtctac atgggcaaga attccaatat tgattatttt | 1920 |
| catgtgattg tcctcccttt actgccccga agggcataaa aatccccagc agtaaaatac | 1980 |
| ttttaccact ggggatgata atttgcggac atacacatat acagcataca cctgtttgtg | 2040 |
| agtgctgttt tggggatat gtcaaaattg ataaggcaaa agtattctta aattgggtac | 2100 |
| aaaaaactaa gccctacaa aagggactat cataatcctt tgttcccact atttgattat | 2160 |
| agttttattt aaggcaacac cgcacaaatg ccacaatccg cattatacag caggtgccga | 2220 |
| ataaaaactg tggataacct ccgaattttt tgtccgcaaa ggcgcactga ctcaagctgc | 2280 |
| cagacagggt ctgtcagcca gaatcagatt tgccaacgca acatgatat tgaatttggc | 2340 |
| ttgttgcttt tcaagccctc ggtatcgcgt ttttcggaag cgcagctgct tcttaacgac | 2400 |
| accgaataca tgctctactt tgctcgcac tgaggatttc gcccgttccg ctttctttgc | 2460 |
| tgcgtactgc ccgcttttgc tcagtttctt catctgcgat ggacgacgat tgatcttgta | 2520 |
| cttgattttc cggccagctt tgtttcggac tacggcatct tcgcgcttac ctgcgccgag | 2580 |
| ataaccgctg tctccataga ctgtttcttc ctctcccgtc aataatttcg gcacttccgc | 2640 |
| aacgtcgtgg acatttgccg gtgtagcttc cactgtgtga accagtccgc tgtccttgtc | 2700 |
| cacgccgata tgcgctttgt acccaaagtg ccaggtgttg cccttcttga cttggtgggc | 2760 |
| atccggatcc cgtttctttt ccttattctt ggtagaagag ggggcggaaa tgatggtgga | 2820 |
| atctacaatg gtgcccttt tcagaatgag gccacgttcc atgagcgctg ctaccacctg | 2880 |
| agcgaacagc ttctcctgca gtccgttctt gatcagcaag ttccggaacc ggccaagagt | 2940 |
| atccccgttc ggaacctggt tgctggaatc gacgccgcag aactccgaaa atgcgcggct | 3000 |
| gtcgatggct tctgccaccg tggcctcgtc actcaggtca tagaggtttt gcagcagata | 3060 |
| cagtcggagc atgatctcca gcggataggg tttgttgccg cgctctcctt tgtaatagca | 3120 |
| cggctgaatc atggcaagcc attccttcca cgggacgatc cgttcaatct ggtcgagaaa | 3180 |
| tgctttttc ttcgtccgca cctgtgccag ttcgtcgctg aatgcggaaa tcgtcatctg | 3240 |